(12) United States Patent
Campbell et al.

(10) Patent No.: US 7,825,139 B2
(45) Date of Patent: Nov. 2, 2010

(54) COMPOUNDS AND METHODS FOR SELECTIVE INHIBITION OF DIPEPTIDYL PEPTIDASE-IV

(75) Inventors: David Alan Campbell, Sand Diego, CA (US); David T. Winn, San Diego, CA (US); Juan Manuel Betancort, San Diego, CA (US)

(73) Assignee: Forest Laboratories Holdings Limited (BM)

( * ) Notice: Subject to any disclaimer, the term of this patent is extended or adjusted under 35 U.S.C. 154(b) by 1094 days.

(21) Appl. No.: 11/420,273

(22) Filed: May 25, 2006

(65) Prior Publication Data
US 2006/0276410 A1    Dec. 7, 2006

Related U.S. Application Data

(60) Provisional application No. 60/684,464, filed on May 25, 2005.

(51) Int. Cl.
*A61K 31/445* (2006.01)
*C07D 401/14* (2006.01)

(52) U.S. Cl. .................. 514/326; 546/208
(58) Field of Classification Search .............. 546/208; 514/326
See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,572,912 A | 2/1986 | Yoshioka et al. |
| 4,681,893 A | 7/1987 | Roth |
| 4,759,923 A | 7/1988 | Buntin et al. |
| 4,871,721 A | 10/1989 | Biller |
| 4,924,024 A | 5/1990 | Biller |
| 4,935,493 A | 6/1990 | Bachovchin et al. |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,346,701 A | 9/1994 | Heiber et al. |
| 5,354,772 A | 10/1994 | Kathawala |
| 5,385,929 A | 1/1995 | Bjorge et al. |
| 5,447,954 A | 9/1995 | Gribble et al. |
| 5,462,928 A | 10/1995 | Bachovchin et al. |
| 5,488,064 A | 1/1996 | Sher |
| 5,491,134 A | 2/1996 | Sher et al. |
| 5,541,204 A | 7/1996 | Sher et al. |
| 5,574,017 A | 11/1996 | Gutheil |
| 5,594,016 A | 1/1997 | Ueno et al. |
| 5,595,872 A | 1/1997 | Wetterau, II et al. |
| 5,614,492 A | 3/1997 | Habener |
| 5,631,224 A | 5/1997 | Efendic et al. |
| 5,686,104 A | 11/1997 | Mills et al. |
| 5,712,279 A | 1/1998 | Biller et al. |
| 5,712,396 A | 1/1998 | Magnin et al. |
| 5,739,135 A | 4/1998 | Biller et al. |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson, Jr. et al. |
| 5,885,983 A | 3/1999 | Biller et al. |
| 5,952,301 A | 9/1999 | Drucker |
| 5,952,322 A | 9/1999 | Hoover et al. |
| 5,962,440 A | 10/1999 | Sulsky |
| 5,965,532 A | 10/1999 | Bachovchin |
| 5,998,463 A | 12/1999 | Hulin et al. |
| 6,011,155 A | 1/2000 | Villhauer |
| 6,040,145 A | 3/2000 | Huber et al. |
| 6,107,317 A | 8/2000 | Villhauer |
| 6,110,949 A | 8/2000 | Villhauer |
| 6,124,305 A | 9/2000 | Villhauer |
| 6,166,063 A | 12/2000 | Villhauer |
| 6,172,081 B1 | 1/2001 | Damon |
| 6,258,597 B1 | 7/2001 | Bachovchin et al. |
| 6,300,314 B1 | 10/2001 | Wallner et al. |

(Continued)

FOREIGN PATENT DOCUMENTS

EP    0818448 B1    1/1998

(Continued)

OTHER PUBLICATIONS

"Avasimibe: Treatment of Lipoprotein Disorders, ACAT Inhibitor", *Drugs of the Future* 24(1), (1999), 9-15.

(Continued)

*Primary Examiner*—Celia Chang
(74) *Attorney, Agent, or Firm*—David M. Mott

(57) ABSTRACT

Compounds that selectively inhibit dipeptidyl peptidase-IV over closely related dipeptidyl peptidases are those of Formula (I):

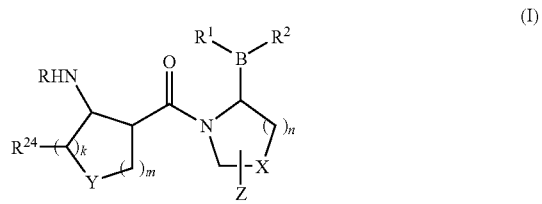

as well as pharmaceutically acceptable salts thereof, cyclic isomers thereof, prodrugs thereof, and solvates thereof, where all the variables are defined herein. These compounds can be used, alone or in combination with other drugs, for the treatment of diabetes and related diseases.

18 Claims, No Drawings

U.S. PATENT DOCUMENTS

| | | | |
|---|---|---|---|
| 6,303,661 | B1 | 10/2001 | Demuth et al. |
| 6,355,614 | B1 | 3/2002 | Wallner |
| 6,380,398 | B2 | 4/2002 | Kanstrup et al. |
| 6,395,767 | B2 | 5/2002 | Robl et al. |
| 6,432,969 | B1 | 8/2002 | Villhauer |
| 6,617,340 | B1 | 9/2003 | Villhauer |
| 6,989,402 | B1 | 1/2006 | Hangeland et al. |
| 7,317,109 | B2 | 1/2008 | Campbell et al. |
| 2003/0100563 | A1 | 5/2003 | Edmondson et al. |
| 2003/0153509 | A1 | 8/2003 | Bachovchin et al. |
| 2006/0258621 | A1 | 11/2006 | Campbell et al. |
| 2006/0264400 | A1 | 11/2006 | Campbell et al. |
| 2006/0264401 | A1 | 11/2006 | Campbell et al. |
| 2007/0185061 | A1* | 8/2007 | Campbell et al. ............ 514/64 |
| 2007/0299036 | A1 | 12/2007 | Campbell et al. |
| 2008/0182995 | A1 | 7/2008 | Campbell et al. |

FOREIGN PATENT DOCUMENTS

| | | |
|---|---|---|
| EP | 0896538 B1 | 2/1999 |
| EP | 0978279 A1 | 2/2000 |
| EP | 1041068 B1 | 4/2004 |
| KR | 20060121170 | 11/2006 |
| WO | WO-89/03223 A1 | 4/1989 |
| WO | WO-91/16339 A1 | 10/1991 |
| WO | WO-93/08259 A2 | 4/1993 |
| WO | WO-93/10127 A1 | 5/1993 |
| WO | WO-95/11689 A1 | 5/1995 |
| WO | WO-95/15309 A1 | 6/1995 |
| WO | WO-96/39384 A1 | 12/1996 |
| WO | WO-96/39385 A1 | 12/1996 |
| WO | WO-97/12613 A1 | 4/1997 |
| WO | WO-97/12615 A1 | 4/1997 |
| WO | WO-97/21993 A2 | 6/1997 |
| WO | WO-98/00439 A2 | 1/1998 |
| WO | WO-98/19998 A2 | 5/1998 |
| WO | WO-98/50046 A1 | 11/1998 |
| WO | WO-99/00353 A1 | 1/1999 |
| WO | WO-99/03850 A1 | 1/1999 |
| WO | WO-99/26659 A1 | 6/1999 |
| WO | WO-99/38501 A2 | 8/1999 |
| WO | WO-99/43663 A1 | 9/1999 |
| WO | WO-00/34241 A1 | 6/2000 |
| WO | WO-00/38722 A1 | 7/2000 |
| WO | WO-00/47206 A1 | 8/2000 |
| WO | WO-03/045228 A2 | 6/2003 |
| WO | WO-03/045977 A2 | 6/2003 |
| WO | WO-2004/004661 A2 | 1/2004 |
| WO | WO-2004044661 A3 | 5/2004 |
| WO | WO 2005/047297 * | 5/2005 |
| WO | WO-2005047297 A1 | 5/2005 |
| WO | WO-2005075426 A1 | 8/2005 |
| WO | WO-2006040625 A1 | 4/2006 |

OTHER PUBLICATIONS

"International Search Report and Written Opinion for PTC Application No. PCT/US04/37820", (Mar. 10, 2005), 9 pgs.

Bachovchin, W. W., et al., "Inhibition of IgA1 Proteinases from *Neisseria gonorrhoeae* and *Hemophilus influenzae* by Peptide Prolyl Boronic Acids", *Journal of Biological Chemistry*. 265(7), (Mar. 5, 1990), 3738-3743.

Balkan, B., et al., "Improved Insulin Secretion and Oral Glucose Tolerance after in Vivo Inhibition of DPP-IV in Obese Zucker Rats", *Diabetologia*, Sugol. 40, A131 Abstract, (1977),1 page.

Biller, S. A., et al., "Communications to the Editor: Isoprenoid (Phosphinylmethyl)phosphonates as Inhibitors of Squalene Synthetase", *Journal of Medicinal Chemistry*, 31(10), (Oct. 1988), 1869-1871.

Biller, S. A., "Squalene Synthase Inhibitors", *Current Pharmaceutical Design*, 2(1), (1996), 1-40.

Corey, E. J., "Application of Unreactive Analogs of Terpenoid Pyrophosphates to Studies of Multistep Biosynthesis. Demonstration That "Presqualene Pyrophosphate" Is an Essential Intermediate on the Path to Squalene", *Journal of the American Chemical Society*, 98(5). (1976), 1291-1293.

Coutts, S. J., "Structure-Activity Relationships of Boronic Acid Inhibitors of Dipeptidyl Peptidase IV. 1. Variation of the $P_2$ Position of $X_{aa}$-boroPro Dipeptides", *J. Med. Chem.* 39(10), (1996), 2087-2094.

Coutts, S. J., et al., "Two Efficient Methods for the Cleavage of Pinanediol boronate Esters Yielding the Free Boronic Acids", *Tetrahedron Letters*, 35(29), (1994),5109-5112.

Deacon, C. F., et al., "Both Subcutaneously and Intravenously Administered Glucagon-Like Peptide I are Rapidly Degraded From the $NH_2$-Terminus in Type II Diabetic Patients and in Healthy Subjects", *Diabetes*, 44(9), Retrieved from the Internet: <http://gateway.ut.ovid.com.floyd.lib.umn.edu/gw2/ovidweb.cgi>, (1995), 1126-1131, (11 pgs.).

Deacon, C. F., et al., "Dipeptidyl Peptidase IV Inhibition as an Approach to the Treatment and Prevention of Type 2 Diabetes: A Historical Perspective", *Biochemical and Biophysical Research Communications 294*, (2002), 1-4.

Demuth, H.-U., et al., "Rebuttal to Deacon and Holst: "Metformin Effects on Dipeptidyl Peptidase IV Degradation of Glucagon-like Peptide-1" Versus "Dipeptidyl Peptidase Inhibition as an Approach to the Treatment and Prevention of Type 2 Diabetes: a Historical Perspective"", *Biochemical and Biophysical Research Communications 296*, (2002), 229-232.

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", *Cardiovascular Drug Reviews*, 16(1), (1998), 16-30.

Hara, S., "Ileal $Na^+$/bile Acid Cotransporter Inhibitors", *Drugs of the Future*, 24(4), (1999), 425-430.

Hinke, S. A., et al., "Metformin Effects on Dipeptidyl-Peptidase IV Degradation of Glucagon-like Peptide-1", *Biochemical and Biophysical Research Communications 291*, (2002), 1302-1308.

Holst, Jens J., et al., "Perspectives in Diabetes: Inhibition of the Activity of Dipeptidyl-Peptidase IV as a Treatment for Type 2 Diabetes", *Diabetes*, vol. 47, From the Department of Medical Physiology, University of Copenhagen, Copenhagen, Denmark, (Nov. 1998), 1663-1670.

Kelly, T. A., et al., "Immunosuppresive Boronic Acid Dipeptides Correlation Between Conformation and Activity", *Journal of the American Chemical Society*, 115(26), (1993), 12637-12638.

Krause, B. R., "ACAT Inhibitors: Physiologic Mechanisms for Hypolipidemic and Anti-Atherosclerotic Activities in Experimental Animals", *Inflammation: Mediators and Pathways*, Ruffolo, Jr., et al., Editors, published by CRC Press, Boca Raton, FL, (1995), 173-198.

Kubota, T., et al., "Dipeptidyl Peptidase IV (DP IV) Activity in Serum and on Lymphocytes of MRL/Mp-/prllpr Mice correlates With Disease Onset", *Clin Exp Immunol 96*, (1994), 292-296.

McClard, R W., "Novel Phosphonylphosphinyl (P-C-P-C-) Analogues of Biochemically Interesting Diphosphates. Syntheses and Properties of P-C-P-C-Analogues of Isopentenyl Diphosphate and Dimethylallyl Diphosphate", *J. Am. Chem. Soc.*, vol. 109, (1987), 5544-5545.

Murakami, K., "A Novel Insulin Sensitizer Acts as a Coligand for Peroxisome Proliferation—Activated Receptor-α (PPAR-α) and PPAR-γ—Effect on PPAR-α Activation on Abnormal Lipid Metabolism in Liver of Zucker Fatty Rats", *Diabetes*, vol. 47 (Dec. 1998), 1841-1847.

Nicolosi, R. J., et al., "The ACAT Inhibitor, CI-1011 is Effective in the Prevention and Regression of Aortic Fatty Streak Area in Hamsters", *Atherosclerosis 137*, (1998),77-85.

Ortiz De Montellano, P. R., "Inhibition of Squalene Synthetase by Farnesyl Pyrophosphate Analogues", *Journal of Medicinal Chemistry*, 20(2), (1977), 243-249.

Pauly, R. P., et al., "Inhibition of Dipeptidyl Peptidase IV (DP IV) in Rat Results in Improved Glucose Tolerance", *Abstracts from the 11th International Symposium on Regulatory Peptides*, (1996), p. 148.

Rosenblum, S. B., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", *J. Med. Chem. 41*, (1998), 973-980.

Salisbury, B. G., "Hypocholesterolemic Activity of a Novel Inhibitor of Cholesterol Absorption, SCH 48461", *Atherosclerosis 115*, (1995), 45-63.

Sendobry, S. M., "Attenuation of Diet-Induced Atherosclerosis in Rabbits with a Highly Selective 15-lipoxygenase Inhibitor Lacking Significant Antioxidant Properties", *British Journal of Pharmacology 120*, (1997), 1199-1206.

Sliskovic, D. R., "ACAT Inhibitors: Potential Anti-atherosclerotic Agents", *Current Medicinal Chemistry*, 1(3), (1994), 204-225.

Smith, C., "RP 73163: A Bioavailable Alkylsulphinyl-Diphenylimidazole ACAT Inhibitor", *Bioorganic & Medicinal Chemistry Letters*, 6(1), (1996), 47-50.

Stout, D. M., et al., "Inhibitors of Acyl-CoA: Cholesterol O-Acyl Transferase (ACAT) as Hypocholesterolemic Agents. 6. The First Water-Soluble ACAT Inhibitor With Lipid-Regulating Activity", *Chemtracts-Organic Chemistry*, vol. 8, (1995), 359-362.

Tanaka, S., et al., "Suppression of Arthritis by the Inhibitors of Dipeptidyl Peptidase IV", *International Journal of Immunopharmacology*, 19(1), (1997), 15-24.

Tanaka, S., et al., "Suppression of Arthritis by the Inhibitors of Dipeptidyl Peptidase IV", *Ensho—Japanese Journal of Inflammation*, 18(3), (1998), 199-202.

"U.S. Appl. No. 10/514,575, Preliminary Amendment filed Nov. 6, 2006", 19 pgs.

"U.S. Appl. No. 10/514,575, Response filed Sep. 17, 2008 to Restriction Requirement mailed Aug. 19, 2008", 21 pgs.

"U.S. Appl. No. 10/514,575, Restriction Requirement mailed Aug. 19, 2008", 11 pgs.

"U.S. Appl. No. 10/514,575, Supplemental Preliminary Amendment Nov. 13, 2006", 21 pgs.

"U.S. Appl. No. 11/556,944, Preliminary Amendment mailed Jul. 15, 2008", 9 pgs.

"International Application Serial No. PCT/US04/37820, International Search Report mailed Mar. 10, 2005", 5 pgs.

"International Application Serial No. PCT/US04/37820, Written Opinion mailed Mar. 10, 2005", 4 pgs.

Flentke, G. R., et al., "Inhibition of dipeptidyl aminopeptidase IV (DP-IV) by Xaa-boroPro dipeptides and use of these inhibitors to examine the role of DP-IV in T-cell function", *PNAS*, USA, 88,, abstract obtained from CAPLUS database, accession No. 114:205351, (1991), 2 pgs.

"U.S. Appl. No. 10/514,575, Non-Final Office Action mailed Dec. 29, 2008", 17 pgs.

"U.S. Appl. No. 10/514,575, Response filed Mar. 23, 2009 to Non Final Office Action mailed Dec. 29, 2008", 31 pgs.

"U.S. Appl. No. 11/381,082, Final Office Action mailed Sep. 19, 2008", 14 pgs.

"U.S. Appl. No. 11/381,082, Non-Final Office Action mailed Mar. 17, 2008", 15 pgs.

"U.S. Appl. No. 11/381,082, Notice of Allowance mailed Apr. 17, 2009", 7 pgs.

"U.S. Appl. No. 11/381,082, Notice of Allowance mailed Dec. 31, 2008", 7 pgs.

"U.S. Appl. No. 11/381,082, Response filed Jun. 17, 2008 to Non Final Office Action mailed Mar. 17, 2008", 21 pgs.

"U.S. Appl. No. 11/381,082, Response filed Nov. 19, 2008 to Final Office Action mailed Sep. 19, 2008", 26 pgs.

"U.S. Appl. No. 11/381,085, Non-Final Office Action mailed Aug. 1, 2007", 9 pgs.

"U.S. Appl. No. 11/381,085, Notice of Allowance mailed Oct. 11, 2007", 4 pgs.

"U.S. Appl. No. 11/381,085, Response filed May 2, 2007 to Restriction Requirement mailed Apr. 2, 2007", 13 pgs.

"U.S. Appl. No. 11/381,085, Response filed Sep. 13, 2007 to Non-Final Office Action mailed Aug. 1, 2007", 9 pgs.

"U.S. Appl. No. 11/381,085, Restriction Requirement mailed Apr. 2, 2007", 12 pgs.

"U.S. Appl. No. 11/381,090, Final Office Action mailed Dec. 22, 2008", 11 pgs.

"U.S. Appl. No. 11/381,090, Non-Final Office Action mailed Jun. 26, 2008", 11 pgs.

"U.S. Appl. No. 11/381,090, Response filed Mar. 17, 2008 to Restriction Requirement mailed Feb. 19, 2008", 3 pgs.

"U.S. Appl. No. 11/381,090, Response filed Mar. 20, 2009 to Final Office Action mailed Dec. 22, 2009", 13 pgs.

"U.S. Appl. No. 11/381,090, Response filed Sep. 23, 2008 to Non Final Office Action mailed Jun. 26, 2008", 25 pgs.

"U.S. Appl. No. 11/381,090, Restriction Requirement mailed Feb. 19, 2008", 12 pgs.

"International Application Serial No. 04810839.3, Non-Final Office Action mailed Jul. 18, 2007", 4 pgs.

"International Application Serial No. 04810839.3, Supplemental European Search Report mailed Dec. 13, 2006", 3 pgs.

"International Application Serial No. 06015708.8-2177, Extended European Search Report mailed Dec. 13, 2006", 16 pgs.

"International Application Serial No. 200603077-9, Non-Final Office Action mailed Mar. 24, 2008", 4 pgs.

"International Application Serial No. 200603077-9, Non-Final Office Action mailed May 29, 2007", 4 pgs.

"Korean Application Serial No. 10-2006-7011419, Office Action mailed May 16, 2008", 10 pgs.

"Point Therapeutics", http://www.pther.com, http://web.archive.org/web/20070827113729/http://www.pther.com/.

Augustyns, K., et al., "The unique properties of dipeptidyl-peptidase IV (DPP IV / CD26) and the therapeutic potential of DPP IV inhibitors", *Curr Med Chem.*, 6(4), (Apr. 1999), 311-27.

Balkan, B., et al., "Inhibition of dipeptidyl peptidase IV with NVP-DPP728 increases plasma GLP-1 (7-36 amide) concentrations and improves oral glucose tolerance in obese Zucker rats.", *Diabetologia*, 42(11), (Nov. 1999), 1324-31.

Chen, W. T, "DPPIV and seprase in cancer invasion and angiogenesis.", *Adv Exp Med Biol.*, 524, (2003), 197-203.

Conarello, S. L, et al., "Mice lacking dipeptidyl peptidase IV are protected against obesity and insulin resistance.", *Proc Natl Acad Sci U S A.*, 100(11), (May 27, 2003), 6825-30.

Dang, N. H, et al., "CD26: an expanding role in immune regulation and cancer.", *Histol Histopathol.*, 17(41, (Oct. 2002), 1213-26.

Hughes, T. E. et al., "NVP-DPP728 (1-[[[2-[(5-cyanopyridin-2-yl)amino]ethyl]amino]acetyl]-2-cyano-(S)- pyrrolidine), a slow-binding inhibitor of dipeptidyl peptidase IV.", *Biochemistry*, 38(36), (Sep. 7, 1999), 11597-603.

Kirkpatrick, P., "Giving nature a helping hand", *Nature Reviews Drug Discovery*,Jul. 2002, 1. (Jul. 2004), 486-487.

Lambeir, A M, et al., "Kinetic investigation of chemokine truncation by CD26/dipeptidyl peptidase IV reveals a striking selectivity within the chemokine family", *J Biol Chem.*, 276(32), (Aug. 10, 2001), 29839-45.

Marighetto, A, et al., "Further evidence for a dissociation between different forms of mnemonic expressions in a mouse model of age-related cognitive decline: effects of tacrine and S 17092, a novel prolyl endopeptidase inhibitor.", *Learn Mem.*, 7(3), (May-Jun. 2000), 159-69.

Mentlein, R. "Dipeptidyl-peptidase IV (CD26)—role in the inactivation of regulatory peptides.", *Regul Pept.*, 85(1), (Nov. 30, 1999), 9-24.

Morain, P., et al., "Pharmacodynamic and pharmacokinetic profile of S 17092, a new orally active prolyl endopeptidase inhibitor, in elderly healthy volunteers. A phase I study.", *Br J Clin Pharmacol.*, 50(4), (Oct. 2000), 350-9.

Morissette, S. L, et al., "High-throughput crystallization: polymorphs,salts,co-crystals and solvates of pharmaceutical solids", *Advanced Drug Delivery Reviews 2004*,56., (2004), 275-300.

Pederson, R. A. et al., "Improved glucose tolerance in Zucker fatty rats by oral administration of the dipeptidyl peptidase IV inhibitor isoleucine thiazolidide.", *Diabetes 47*(8), (Aug. 1998), 1253-8.

Pospisilik, J. A, et al., "Dipeptidyl peptidase IV inhibitor treatment stimulates beta-cell survival and islet neogenesis in streptozotocin-induced diabetic rats.", *Diabetes*, 52(3), (Mar. 2003), 741-50.

Sedo, A., et al., "Dipeptidyl peptidase IV-like molecules: homologous proteins or homologous activities?", *Biochim Biophys Acta.*, 1550(2), (Dec. 17, 2001), 107-16.

Sudre, B., et al., "Chronic inhibition of circulating dipeptidyl peptidase IV by FE 999011 delays the occurrence of diabetes in male zucker diabetic fatty rats.", *Diabetes*, 51(5), (May 2002), 1461-9.

Umemura, K., et al., "Pharmacokinetics and safety of Z-321, a novel specific orally active prolyl endopeptidase inhibitor, in healthy male volunteers.", *J Clin Pharmacol.*, 39(5), (May 1999), 462-70.

Van Damme, J., et al., "The role of CD26/DPP IV in chemokine processing.", *Chem. Immunol.*, 72, (1999), 42-56.

Vanhoof. G., et al., "Proline motifs in peptides and their biological processing.", *FASEB J.*, 9(9), (Jun. 1995), 736-44.

* cited by examiner

COMPOUNDS AND METHODS FOR SELECTIVE INHIBITION OF DIPEPTIDYL PEPTIDASE-IV

CROSS REFERENCE TO RELATED APPLICATIONS

This application claims priority to U.S. provisional application No. 60/684,464, filed on May 25, 2005, the entirety of which is incorporated herein by reference. This application is related to U.S. application Ser. No. 10/514,575, filed on Nov. 12, 2004, which is a national stage application of PCT/US04/037820, filed on Nov. 12, 2004, which claims priority to U.S. provisional application No. 60/519,566, filed on Nov. 12, 2003.

FIELD OF THE INVENTION

The present invention relates to boronic acid compounds and their use as selective inhibitors of post-proline/alanine cleaving amino-dipeptidases, particularly dipeptidyl peptidase-IV (DPP-IV). The invention also relates to methodology for employing such inhibitors, alone or with another agent, to treat a DPP-IV-related disease, such as Type II diabetes and diabetic complications, hyperglycemia, or hyperinsulinemia. Thus, the invention has applications in the medicinal chemical, pharmacological, and medical fields.

BACKGROUND OF THE INVENTION

Dipeptidyl peptidase-IV (DPP-IV) is a serine protease that belongs to a group of post-proline/alanine cleaving amino-dipeptidases. DPP-IV catalyzes the release of an N-terminal dipeptide only from proteins with N-terminal penultimate proline or alanine.

The physiological role of DPP-IV has not been established fully. It is believed to play an important role in neuropeptide metabolism, T-cell activation, gastric ulceration, functional dyspepsia, obesity, appetite regulation, impaired fasting glucose (IFG), and diabetes. In particular, DPP-IV has been implicated in the control of glucose metabolism because its substrates include the insulinotropic hormones, glucagon like peptide-1 (GLP-1) and gastric inhibitory peptide (GIP), which are inactivated by removal of their two N-terminal amino acids.

In vivo administration of synthetic inhibitors of DPP-IV prevents N-terminal degradation of insulinotropic hormones including GLP-1 and GIP, resulting in higher plasma concentrations of these hormones, increased insulin secretion and, therefore, improved glucose tolerance. Therefore, such inhibitors have been proposed for the treatment of patients with type II diabetes, a disease characterized by decreased glucose tolerance and insulin resistance.

Other post-proline/alanine cleaving amino-dipeptidases have been discovered, including DPP-VII, DPP-VIII, DPP-IX, and fibroblast activation protein (FAP), that have substrate- and inhibitor-specificity similar to DPP-IV. Thus, inhibitors of this sort may affect multiple members of the enzyme group. The precise physiological role of each of these post-proline/alanine cleaving enzymes is not well defined. However, some evidence exists that non-selective inhibitors of DPP-IV which also inhibit DPP-VIII cause toxic effects in animals.

Accordingly, a need exists for compounds that are useful for inhibiting DPP-IV without an adverse event profile that precludes chronic administration.

Several compounds have been shown to inhibit DPP-IV, but all of these have limitations in relation to the potency, stability, selectivity, toxicity, and/or pharmacodynamic properties. Such compounds have been disclosed, for example, in WO 98/19998, WO 00/34241, U.S. Pat. No. 6,124,305 (Novartis AG), and WO 99/38501 (Trustees of Tufts University).

SUMMARY OF THE INVENTION

The present invention is directed to a selective DPP-IV inhibitor and methods of use that are effective in treating conditions that may be regulated or normalized by inhibition of DPP-IV. More particularly, the invention is directed to a cyclic beta-amino acyl pyrrolidine boronic acid compound. This cyclic beta-amino acyl pyrrolidine boronic acid compound (hereinafter cyclic beta compound) is useful at effective doses for treatment of malconditions associated with DPP-IV activity and is a selective inhibitor of DPP-IV.

A cyclic beta compound of the invention has a structure represented in part by Formula I:

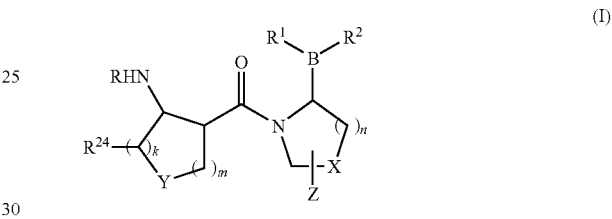

The substituents and bond designations of formula I include $R^1$ and $R^2$, which, independently or together, are —OH, —O⁻ M⁺ wherein M⁺ is a cation, a hydroxyl bearing a boronic acid protecting group, or a group capable of being hydrolyzed to a hydroxyl group in an aqueous solution at physiological pH or in biological fluids. Also included within the scope of the invention are a cyclic isomer thereof, any pharmaceutically acceptable salt thereof, any prodrug thereof, and any solvate thereof. The additional substituents of the cyclic beta compounds of formula I are described below.

More specifically, in accordance with another aspect of the invention, there are provided a group of cyclic beta compounds having the Formula (II):

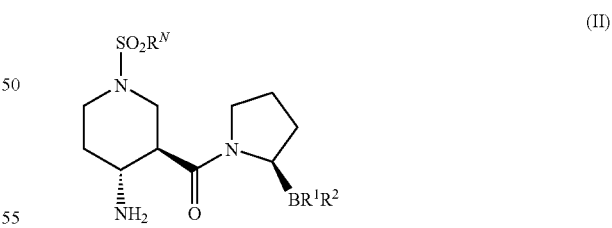

pharmaceutically acceptable salts thereof, hydrates thereof, prodrugs thereof, solvates thereof, and stereomeric mixtures thereof. Preferably, the compound of Formula (II) is 90 wt % or more of a single enantiomer. In other embodiments, the compounds of Formula (II) are 91, 92, 93, 94, 95, 96, 97, 98, or 99 wt % or more of a single enantiomer.

$R^1$ and $R^2$ are as defined for the cyclic beta compound of Formula (I), and $R^N$ is a substituted or unsubstituted alkyl, alkenyl, aryl, aralkyl, cycloalkyl, cycloalkylalkyl, cycloalkenyl, cycloalkenylalkyl, heterocyclyl, or heterocyclylalkyl group wherein $R^N$ is optionally mono- or independently di- or independently trisubstituted with $R^{12}$, as is defined below. For example, $R^N$ can be a substituted phenyl group or a substituted or unsubstituted methyl, ethyl, n-propyl, isopropyl, n-butyl, isobutyl, sec-butyl, biphenyl, or naphthyl group. Exemplary $R^N$ groups include but are not limited to a 4-fluorophenyl, 3-fluorophenyl, 2-fluorophenyl, 2,4-difluorophenyl, 2,4,5-trifluorophenyl, or 4-methylsulfonylphenyl group.

The invention is also directed to a pharmaceutical composition containing a cyclic beta compound of the invention and a pharmaceutical carrier. The pharmaceutical composition may be formulated to be dosed by any administrative route including but not limited to parenteral injection, oral, buccal, rectal and the like.

The invention is also directed to a method of treatment of a malcondition that can be regulated or normalized via inhibition of DPP-IV. The method involves administration of an effective amount of a cyclic beta compound of the invention, such as would be present in a pharmaceutical composition of the invention, to mammals, especially humans, to affect a malcondition that can be regulated or normalized via inhibition of DPP-IV. Preferably, an effective amount of a cyclic beta compound of the invention exhibits lower toxicity than do non-selective inhibitors of DPP-IV, particularly in comparison to boronic acid inhibitors of DPP-IV that also display inhibition of other DPP enzymes Therefore, the invention is directed to methods for selectively inhibiting DPP-IV including administering to a patient in need of such treatment a therapeutically effective amount of a cyclic beta compound of the invention.

The invention further is directed to a pharmaceutical combination of a cyclic beta compound of the invention and one or more other medicaments that are useful for treatment of a malcondition that can be regulated or normalized via inhibition of DPP-IV. Such malconditions are associated with impairments in glycemic control especially Diabetes Mellitus and related conditions. A pharmaceutical combination may be formulated according to the invention as a pharmaceutical composition.

The invention is also directed to a process for preparing a cyclic beta compound of the invention, a method for preparing a pharmaceutical composition of the invention, and the use of a cyclic beta compound of the invention in a method for the preparation of a medicament for treating a malcondition that can be regulated or normalized via inhibition of DPP-IV.

DETAILED DESCRIPTION OF THE INVENTION

Definitions

The term "asymmetric carbon" means a carbon atom covalently bound to four different groups. The term "absolute configuration" in connection with an asymmetric carbon is determined by considering the tetrahedral shape of the asymmetric carbon bonds, assigning a priority of 1 through 4 to each of the groups bound to the asymmetric carbon with the group having the highest atomic number having the first priority. If the tetrahedron is viewed from a side remote from group 4, an R absolute configuration is assigned when groups 1-3 are in a clockwise arrangement and an S absolute configuration is assigned when groups 1-3 are in a counterclockwise arrangement.

The term "enantiomer" means one member of a pair of stereoisomers having the same molecular structure and at least one asymmetric carbon such that the stereoisomers of the pair are the mirror images of each other. If the enantiomer contains two or more asymmetric carbons, the enantiomeric pair will have opposing asymmetry at each asymmetric carbon.

The term "diastereomer" means one member of a group of two or more stereoisomers having at least two asymmetric carbons such that these stereoisomers are not mirror images of each other.

The term "optically active" means an organic compound containing at least one asymmetric carbon such that a solution of the organic compound will rotate plane polarized light. The term "optically active mixture" means a mixture of optically active compounds in solution that will rotate plane polarized light. The optically active mixture may be a mixture of diastereomers or an unequal mixture of enantiomers.

The term "racemic mixture" means an enantiomeric pair of equal proportions such that they cancel each other's rotation of plane polarized light.

A singular term such as "a cyclic beta compound of the invention" includes the plural such as the various species of the cyclic beta compounds of the invention as well as mixtures thereof. A plural term such as "cyclic beta compounds of the invention" includes the individual species as well as the plural indicated by this term, and also mixtures thereof.

The term "selectivity ratio" refers to the $IC_{50}$ value generated in a biochemical assay measuring inhibition of DPP-IV compared to the $IC_{50}$ value generated in a biochemical assay measuring inhibition of another DPP family member (e.g. DPP-VII, DPP-VIII, DPP-IX or FAP) whereby the ratio is obtained by dividing the $IC_{50}$ value of DPP-VII, DPP-VIII, DPP-IX or FAP by the $IC_{50}$ value for DPP-IV.

The term "beta cell degeneration" is intended to mean loss of beta cell function, beta cell dysfunction, and death of beta cells, such as necrosis or apoptosis of beta cells.

The term "Diabetes Mellitus and related conditions" refers to Type 1 diabetes, Type 2 diabetes, gestational diabetes, MODY, impaired glucose tolerance, impaired fasting glucose, hyperglycemia, impaired glucose metabolism, insulin resistance, obesity, diabetic complications, and the like.

The term "diabetic complications" refers to conditions, diseases and maladies associated with diabetes including retinopathies, neuropathies, nephropathies, cardiomyopathies, dermopathies, arthrosclerosis, coronary artery disease and other known complications of diabetes.

The terms "DPP-VII, DPP-VIII, DPP-IX and FAP" mean respectively amino dipeptidyl peptidase VII, VIII, IX and fibroblast activation protein. The DPP enzymes cleave dipeptide moieties at the N-terminus of their protein or oligopeptide substrates. In particular, the term "DPP-IV" denotes dipeptidyl peptidase IV (EC 3.4.14.5; DPP-IV), also known as "CD-26." DPP-IV preferentially cleaves a dipeptide from the N terminus of a polypeptide chain containing a proline or alanine residue in the penultimate position.

The term "inhibitor" (and its corresponding verb and gerund) means a compound that will reversibly, irreversibly or temporarily interact with an enzyme so as to reduce, modify, slow down or block its enzymatic activity upon its normal substrate. The interaction may occur within or at the enzymatic site or at an allosteric site associated with the enzyme.

The term "other type(s) of therapeutic agents" as employed herein refers to one or more antidiabetic agents (other than DPP-IV inhibitors of the invention).

The term "treatment" is defined as the management and care of a patient for the purpose of combating the disease, condition, or disorder and includes administering a compound of the present invention to prevent the onset of the symptoms or complications, or alleviating the symptoms or complications, or eliminating the disease, condition, or disorder.

The term "solvate" means a solid, crystalline form of a compound which also incorporates molecules of a solvent into the crystal structure. Organic solvents as well as water are included. Another description of a water solvate is a hydrate or hydrated form.

The term "pharmaceutical salt" means a salt with an inorganic base, organic base (including basic amino acids), inorganic acid, and organic acid (including acidic amino acids). Included as examples of inorganic bases are alkali metals such as lithium, sodium or potassium; alkaline earth metals such as calcium and magnesium or aluminum; and ammonia. Included as examples of organic bases are trimethylamine, triethylamine, pyridine, picoline, ethanolamine, diethanolamine, and triethanolamine. Included as examples of inorganic acids are the instant invention includes, for example, hydrohalogen acids such as hydrochloric acid, hydroboric acid, nitric acid, sulfuric acid, and phosphoric acid. Included as examples of organic acids are mono, di and tri carboxylic or sulfonic acids of 1 to 20 carbons, optionally containing 1 to 6 hydroxyl groups. Included as examples of basic amino acids are arginine, lysine and ornithine. Included as examples of acidic amino acids are aspartic acid and glutamic acid. Further examples of pharmaceutically acceptable salts include the pharmaceutically acceptable salts listed in Journal of Pharmaceutical Science, 66, 2 (1977) which are known to the skilled artisan.

The term "prodrug" means a pharmaceutically acceptable compound that will convert to the active ingredient or an active metabolite thereof upon administration of the prodrug to a living organism, preferably a mammal, more preferably a human. The conversion may occur by enzymatic action, chemical hydrolysis, oxidation, reduction or any other in vivo physiological process for chemical or biochemical reaction.

The term "group that can be hydrolyzed to a hydroxyl" as used herein refers to groups that can be converted to a hydroxyl group in an aqueous solution. In some embodiments, these groups may be hydrolyzed to a hydroxyl at physiological pH, whereas in other embodiments these groups require acidic, alkaline, or other types of catalysts for hydrolysis. In certain embodiments, these groups are employed to mask or otherwise protect the boronic acid functionality of compounds of the invention while reactions involving other functional sites of the compound are carried out. Typically, the boronic acid OH groups are protected as boronic acid esters derived from alcohols such as (+)- or (−)-pinanediol, pinacol, 1,2-dicyclohexylethanediol, 1,2-ethanediol, 2,2-diethanolamine, 1,3-propanediol, 2,3-butanediol, diisopropyl tartrate, 1,4-butanediol, diisopropylethanediol, (S,S,)-5,6-decanediol, 1,1,2-triphenyl-1,2-ethanediol, (2R,3R)-1,4-dimethoxy-1,1,4,4-tetraphenyl-2,3-butanediol, methanol, ethanol, isopropanol, catechol, 1-butanol, and the like. As will be understood by those skilled in the art, alcohols having only a single hydroxy group, such as methanol, form diesters having the structure —B(OR)$_2$ in which R is the organic moiety from the alcohol (e.g., —B(OMe)$_2$). By comparison, diols such as pinacol form cyclic boronic diesters with —B(OH)$_2$ in which the organic moiety (e.g., —C(Me)$_2$—C(Me)$_2$-) is attached to both oxygens.

The term "N-protecting group," "N-blocking group," or "N-protected" as used herein refers to those groups intended to protect the N-terminus of an amino acid or peptide or to protect an amino group against undesirable reactions during synthetic procedures. Commonly used N-protecting groups are disclosed in T. W. Greene, P. G. Wuts, "Protective Groups In Organic Synthesis, 3$^{rd}$ Ed." (John Wiley & Sons, New York (1999)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-di methyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, 9-fluorenylmethyloxycarbonyl (Fmoc), t-butyloxycarbonyl (Boc) and benzyloxycarbonyl (Cbz).

In general, "substituted" refers to an organic group as defined below in which one or more bonds to a hydrogen atom contained therein are replaced by a bond to non-hydrogen or non-carbon atoms such as, but not limited to, a halogen (i.e., F, Cl, Br, and I); an oxygen atom in groups such as hydroxyl groups, alkoxy groups, aryloxy groups, aralkyloxy groups; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, N-oxides, hydrazides, azides, and enamines; and other heteroatoms in various other groups. Substituted alkyl, alkenyl, alkynyl, cycloalkyl, and cycloalkenyl groups as well as other substituted groups also include groups in which one or more bonds to a carbon(s) or hydrogen(s) atom are replaced by one or more bonds, including double or triple bonds, to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups may also be substituted with alkyl, alkenyl, and alkynyl groups as defined below.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, tert-butyl, neopentyl, isopentyl, and 2,2-dimethylpropyl groups. Representative substituted alkyl groups may be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which may be substituted with, for example, amino, hydroxy, cyano, carboxy, nitro, thio, alkoxy, and halogen groups.

Cycloalkylalkyl groups are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups.

Cycloalkenylalkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C (CH$_2$CH$_3$), —CH$_2$C≡CH, —CH$_2$C≡C(CH$_3$), and —CH$_2$C≡C(CH$_2$CH$_3$) among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halogen groups, bonded to one of the ring members. Rather, groups such as tolyl are referred to as substituted aryl groups. Representative substituted aryl groups may be mono-substituted or substituted more than once, such as, but not limited to, 2-, 3-, 4-, 5-, or 6-substituted phenyl or naphthyl groups, which may be substituted with groups such as those listed above.

Aralkyl groups are alkyl groups as defined above in which a hydrogen or carbon bond of an alkyl group is replaced with a bond to an aryl group as defined above. Representative aralkyl groups include benzyl groups and fused (cycloalkylaryl)alkyl groups such as 4-ethyl-indanyl.

Heterocyclyl groups include aromatic and non-aromatic ring compounds containing 3 or more ring members, of which, one or more is a heteroatom such as, but not limited to, N, O, and S. In some embodiments, heterocyclyl groups include 3 to 20 ring members, whereas other such groups have 3 to 15 ring members. The phrase "heterocyclyl group" includes fused ring species including those comprising fused aromatic and non-aromatic groups. The phrase also includes polycyclic ring systems containing a heteroatom such as, but not limited to, quinuclidyl. However, the phrase does not include heterocyclyl groups that have other groups, such as alkyl or halogen groups, bonded to one of the ring members. Rather, these are referred to as "substituted heterocyclyl groups". Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups may be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups". Representative substituted heteroaryl groups may be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroaralkyl groups are alkyl groups as defined above in which a hydrogen or carbon bond of an alkyl group is replaced with a bond to a heteroaryl group as defined above.

The term "alkoxy" refers to an oxygen atom connected to an alkyl group as defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl. Examples include but are not limited to phenoxy, naphthyloxy, and benzyloxy.

The term "alkanoyl", alone or as part of another group, refers to alkyl linked to a carbonyl group.

The term "amine" (or "amino") includes primary, secondary, and tertiary amines having, e.g., the formula —NR$^6$R$^7$. R$^6$ and R$^7$ at each occurrence are independently hydrogen, or a substituted or unsubstituted alkyl, alkenyl, alkynyl, cycloalkyl, cycloalkenyl, aryl, aralkyl, heterocyclyl or heterocyclylalkyl group as defined herein. Amines thus include but are not limited to —NH$_2$, alkylamines, dialkylamines, arylamines, alkylarylamines, diarylamines, aralkylamines, heterocyclylamines and the like.

The term "amide" (or "amido") includes C- and N-amide groups, i.e., —C(O)NR$^8$R$^9$, and —NR$^8$C(O)R$^9$ groups, respectively. R$^8$ and R$^9$ are independently hydrogen, or a substituted or unsubstituted alkyl, alkenyl, alkynyl, cycloalkyl, cycloalkenyl, aryl, arlkyl, heterocyclyl or heterocyclylalkyl group as defined herein. Amide groups therefore include but are not limited to carbamoyl groups (—C(O)NH$_2$) and formamide groups (—NHC(O)H).

The term "halo" or "halogen" includes fluorine, chlorine, bromine and iodine.

The term "urethane" (or "carbamyl") includes N- and O-urethane groups, i.e., —NR$^{10}$C(O)OR$^{11}$ and —OC(O)NR$^{10}$R$^{11}$ groups, respectively. R$^{10}$ and R$^{11}$ are independently hydrogen, or a substituted or unsubstituted alkyl, cycloalkyl, aryl, aralkyl, or heterocyclyl group as defined herein.

The term "sulfonamide" (or "sulfonamido") includes S- and N-sulfonamide groups, i.e., —SO$_2$NR$^{12}$R$^{13}$ and —NR$^{12}$SO$_2$R$^{13}$ groups, respectively. R$^{12}$ and R$^{13}$ are independently hydrogen, or a substituted or unsubstituted alkyl, cycloalkyl, aryl, aralkyl, or heterocyclyl group as defined herein. Sulfonamide groups therefore include but are not limited to sulfamoyl groups (—SO$_2$NH$_2$).

Unless otherwise specifically stated, the definitions of terms for chemical groups, functional groups, moieties and chemical reactions described herein follow the definitions provided in such organic chemistry textbooks and treatises as "Basic Principles of Organic Chemistry", Roberts and Caserio, W. A. Benjamin & Co. New York, N.Y, 1965; "Advanced Organic Chemistry", 4$^{th}$ edition, Jerry March, Wiley Interscience, New York, N.Y. 1992; T. W. Greene, P. G. Wuts, "Protective Groups In Organic Synthesis, 3$^{rd}$ Ed." (John Wiley & Sons, New York (1999), and Hawley's Condensed Chemical Dictionary, 11$^{th}$ Ed., Sax and Lewis, Van Nostrand, Reinhold, New York, N.Y., 1987. Moreover, the definitions for stereochemical terms are based upon "Stereochemistry of Carbon Compounds", Ernest Eliel, McGraw-Hill publisher, New York, N.Y. 1962. The disclosures of these text books are incorporated herein by reference.

Cyclic Beta Compounds of the Invention

Surprisingly, it has been discovered that the cyclic beta compounds of the present invention display marked selectivity for DPP-IV relative to related dipeptidyl peptidase enzymes. By selectivity for DPP-IV it is meant that the compounds more strongly inhibit DPP-IV than at least one closely related enzyme such as DPP-VII, DPP-VIII, DPP-IX and FAP. While not wishing to be bound by any theory, it is believed that this unexpected selectivity for DPP-IV results in an improved therapeutic profile with diminished side-effects compared to previous enzyme inhibitors known in the art and compared to any other non-selective DPP-IV inhibitor. In particular it is believed that potent inhibition of DPP-VIII by previous inhibitors correlates with the acute toxicity observed in animal studies. As detailed in Examples of the present invention, studies in dogs show that inhibition of DPP-VIII appears to cause severe emesis and diarrhea, while studies in rats show that inhibition of DPP-VIII caused death. Inventive compounds avoid significant inhibition of DPP-VIII and therefore avoid side-effects associated with DPP-VIII inhibition.

According to the present invention, there are provided cyclic beta compounds having formula (I):

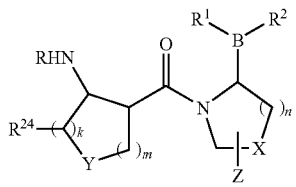

including all cyclic isomers thereof, stereoisomers thereof, solvates thereof, hydrates thereof and pharmaceutically acceptable salts thereof, wherein n is 1 to 3;

X is $CH_2$; S; O; $CF_2$ or $C(CH_3)_2$;

Z is H; halogen; hydroxyl; $(C_{1-6})$alkoxy; $(C_{1-12})$alkyl; $(C_{3-12})$cycloalkyl; phenyl; or heteroaryl; where the phenyl and heteroaryl groups are optionally mono- or independently plurisubstituted with $R^7$;

optionally, X together with an adjacent ring carbon and Z form a fused cyclopropyl; and optionally, one of the bonds in the ring containing X is a double bond;

$R^7$ is halogen, $(C_{1-10})$alkyl, $(C_{1-10})$alkoxy, $(C_{1-10})$alkylamino, $(C_{1-10})$dialkylamino, benzyl, benzyloxy, hydroxy $(C_{1-6})$alkyl, hydroxymethyl, nitro, trifluoromethyl, trifluoromethoxy, trifluoromethylthio, N-hydroxyimino, cyano, carboxy, acetamido, hydroxy, sulfamoyl, sulfonamido, carbamoyl; and $R^{12}$ is halogen; trifluoromethyl; cyano; nitro; $(C_{1-6})$alkyl; $(C_{1-6})$alkoxy; cycloalkyl; carboxy; acetamido; hydroxy; hydroxy$(C_{1-6})$alkyl; hydroxymethyl; trifluoromethoxy; sulfamoyl; carbamoyl; sulfonamido; alkylsulfonyl; phenylsulfonyl; aryl; heteroaryl; where the aryl and heteroaryl groups are optionally mono- or independently plurisubstituted with $R^7$;

Y is O, S, $CHR^{25}$ or $NR^{26}$;

k is 0 to 3 and m is 0 to 3 when Y is $CHR^{25}$;

k is 1 to 3 and m is 0 to 3 when Y is $NR^{26}$;

k is 1 to 3 and m is 0 to 3 when Y is O;

$R^1$ and $R^2$ independently or together are —OH, —$O^-$ $M^+$ wherein $M^+$ is a cation, a hydroxyl bearing a boronic acid protecting group, or a group capable of being hydrolyzed to a hydroxyl group in an aqueous solution at physiological pH or in biological fluids;

R is hydrogen, $(C_{1-12})$alkyl or $(C_{3-12})$ cycloalkyl;

each $R^{24}$ is independently:

a) hydrogen;

b) $(C_{1-12})$alkyl; $(C_{2-12})$alkenyl; $(C_{2-12})$alkynyl; $(C_{3-12})$ cycloalkyl; or $(C_{3-12})$cycloalkenyl; where the alkyl, alkenyl, alkynyl, cycloalkyl and cycloalkenyl groups are optionally mono- or independently plurisubstituted with $R^{12}$, and where the alkyl, alkenyl, alkynyl portions include linear or branched chains and may include cyclic portions;

c) aryl; or heteroaryl; where the aryl and heteroaryl groups are optionally mono- or independently plurisubstituted with $R^{12}$;

d) $R^{11}(CH_2)_p$— where $R^{11}$ is 2-oxopyrrolidinyl; $(C_{1-6})$ alkoxy; phenyl; phenoxy; $(C_{1-8})$cycloalkyl; [3.3.3] bicyclic carbocyclic moiety; pyridinyl; naphthyl; cyclohexenyl; $(C_{1-8})$alkylcarbonyl; $(C_{3-12})$cycloalkylcarbonyl; benzyl; benzoyl; pyrimidinyl; phenylaminocarbonyl; alkylsulfonyl; phenylsulfonyl; or adamantyl; where the cycloalkyl ring is optionally substituted with hydroxy $(C_{1-6})$alkyl; where the 2-oxopyrrolidinyl, $(C_{1-6})$alkoxy, phenyl, pyridinyl, benzyl, benzoyl, pyrimidinyl, phenylaminocarbonyl, alkylsulfonyl, phenylsulfonyl, and naphthyl groups are optionally mono- or independently di- or independently trisubstituted with $R^{12}$; where the phenoxy group is optionally mono- or independently disubstituted with $(C_{1-4})$alkyl, $(C_{1-4})$alkoxy, or halogen; and where the [3.3.3] bicyclic carbocyclic moiety is optionally mono-or independently plurisubstituted with $(C_{1-8})$alkyl; p is 0 to 3;

e) $(R^{13})_2CH(CH_2)_q$—, where $R^{13}$ is phenyl; in which the phenyl groups are independently optionally mono- or independently disubstituted with $R^{12}$; and q is 0 to 3;

f) a group of the formula:

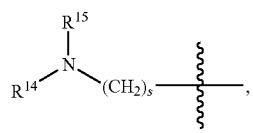

where $R^{14}$ and $R^{15}$ are independently hydrogen; $(C_{1-8})$alkyl; $(C_{1-6})$alkylcarbonyl; $(C_{3-12})$cycloalkyl ring; $(C_{3-12})$cycloalkenyl ring; benzyl; benzoyl; pyridine; pyrimidine; phenyl; phenylaminocarbonyl; alkylsulfonyl; or phenylsulfonyl; where the cycloalkyl ring is optionally substituted with hydroxy$(C_{1-6})$alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a $(C_{3-12})$cycloalkyl ring; and s is 0 to 6; or g) a group of the formula:

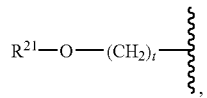

where $R^{21}$ is hydrogen; $(C_{1-8})$alkyl; benzyl; or phenyl; in which the benzyl and phenyl groups are optionally mono- or independently di-substituted on the ring with $R^{12}$; and t is 0 to 6;

$R^{25}$ is:

a) hydrogen;

b) $(C_{1-12})$alkyl; $(C_{2-12})$alkenyl; $(C_{2-12})$alkynyl; $(C_{3-12})$ cycloalkyl; or $(C_{3-12})$cycloalkenyl; where the alkyl, alkenyl, alkynyl, cycloalkyl and cycloalkenyl groups are optionally mono- or independently plurisubstituted with $R^{12}$, and where the alkyl, alkenyl, alkynyl portions include linear or branched chains and may include cyclic portions;

c) aryl; or heteroaryl; where the aryl and heteroaryl groups are optionally mono- or independently plurisubstituted with $R^{12}$;

d) $R^{11}(CH_2)_p$— where $R^{11}$ is 2-oxopyrrolidinyl; $(C_{1-6})$ alkoxy; phenyl; phenoxy; $(C_{1-8})$cycloalkyl; [3.3.3] bicyclic carbocyclic moiety; pyridinyl; naphthyl; cyclohexenyl; $(C_{1-8})$alkylcarbonyl; $(C_{3-12})$cycloalkylcarbonyl; benzyl; benzoyl; pyrimidinyl; phenylaminocarbonyl; alkylsulfonyl; phenylsulfonyl; or adamantyl; where the cycloalkyl ring is optionally substituted with hydroxy ($C_{1-6}$)alkyl; where the 2-oxopyrrolidinyl, ($C_{1-6}$)alkoxy, phenyl, pyridinyl, benzyl, benzoyl, pyrimidinyl, phenylaminocarbonyl, alkylsulfonyl, phenylsulfonyl, and naphthyl groups are optionally mono- or independently di- or independently trisubstituted with $R^{12}$; where the phenoxy group is optionally mono- or independently disubstituted with ($C_{1-4}$)alkyl, ($C_{1-4}$)alkoxy, or halogen; and where the [3.3.3] bicyclic carbocyclic moiety is optionally mono-or independently plurisubstituted with ($C_{1-8}$)alkyl; p is 0 to 3;

e) $(R^{13})_2CH(CH_2)_q$—, where $R^{13}$ is phenyl; in which the phenyl groups are independently optionally mono- or independently disubstituted with $R^{12}$; and q is 0 to 3;

f) a group of the formula:

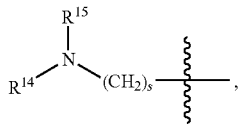

where $R^{14}$ and $R^{15}$ are independently hydrogen; ($C_{1-8}$)alkyl; ($C_{1-6}$)alkylcarbonyl; ($C_{3-12}$)cycloalkyl ring; ($C_{3-12}$)cycloalkenyl ring; benzyl; benzoyl; pyridine; pyrimidine; phenyl; phenylaminocarbonyl; alkylsulfonyl; or phenylsulfonyl; where the cycloalkyl ring is optionally substituted with hydroxy($C_{1-6}$)alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a ($C_{3-12}$)cycloalkyl ring; and s is 0 to 6; or g) a group of the formula:

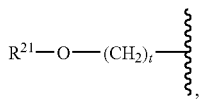

where $R^{21}$ is hydrogen; ($C_{1-8}$)alkyl; benzyl; or phenyl; in which the benzyl and phenyl groups are optionally mono- or independently di-substituted on the ring with $R^{12}$; and t is 0 to 6; and $R^{26}$ is:
a) hydrogen;
b) ($C_{1-12}$)alkyl; ($C_{2-12}$)alkenyl; ($C_{2-12}$)alkynyl; ($C_{3-12}$)cycloalkyl; or ($C_{3-12}$)cycloalkenyl; where the alkyl, alkenyl, alkynyl, cycloalkyl and cycloalkenyl groups are optionally mono- or independently plurisubstituted with $R^{12}$, and where the alkyl, alkenyl, alkynyl portions include linear or branched chains and may include cyclic portions;
c) aryl; or heteroaryl; where the aryl and heteroaryl groups are optionally mono- or independently plurisubstituted with $R^{12}$;
d) $R^{27}(CH_2)_p$—, where $R^{27}$ is 2-oxopyrrolidinyl; ($C_{1-6}$)alkoxy; phenyl; phenoxy; ($C_{1-8}$)cycloalkyl; [3.3.3] bicyclic carbocyclic moiety; pyridinyl; naphthyl; cyclohexenyl; ($C_{1-8}$)alkylcarbonyl; ($C_{3-12}$)cycloalkylcarbonyl; benzyl; benzoyl; pyrimidinyl; phenylaminocarbonyl; $R^NSO_2$— wherein $R^N$ is a substituted or unsubstituted alkyl, alkenyl, aryl, aralkyl, cycloalkyl, cycloalkylalkyl, cycloalkenyl, cycloalkenylalkyl, heterocyclyl, or heterocyclylalkyl group; or adamantyl; where the cycloalkyl ring is optionally substituted with hydroxy ($C_{1-6}$)alkyl; where the 2-oxopyrrolidinyl, ($C_{1-6}$)alkoxy, phenyl, pyridinyl, benzyl, benzoyl, pyrimidinyl, phenylaminocarbonyl, $R^N$, and naphthyl groups are optionally mono- or independently di- or independently trisubstituted with $R^{12}$; where the phenoxy group is optionally mono- or independently disubstituted with ($C_{1-4}$)alkyl, ($C_{1-4}$)alkoxy, or halogen; and where the [3.3.3] bicyclic carbocyclic moiety is optionally mono-or independently plurisubstituted with ($C_{1-8}$)alkyl; p is 0 to 3;

e) $(R^{13})_2CH(CH_2)_q$—, where $R^{13}$ is phenyl, in which the phenyl groups are independently optionally mono- or independently disubstituted with $R^{12}$; and q is 0 to 3;

f) a group of the formula:

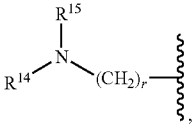

where $R^{14}$ and $R^{15}$ are independently hydrogen; ($C_{1-8}$)alkyl; ($C_{1-6}$)alkylcarbonyl; ($C_{3-12}$)cycloalkyl ring; ($C_{3-12}$)cycloalkenyl ring; benzyl; benzoyl; pyridine; pyrimidine; phenyl; phenylaminocarbonyl; alkylsulfonyl; or phenylsulfonyl; where the cycloalkyl ring is optionally substituted with hydroxy($C_{1-6}$)alkyl, and where the benzyl, benzoyl, pyridine, pyrimidine, phenyl, phenylaminocarbonyl, alkylsulfonyl, and phenylsulfonyl groups are optionally mono- or independently di-substituted with $R^{12}$; or $R^{14}$ and $R^{15}$ together form a ($C_{3-12}$)cycloalkyl ring; and r is 0 or 2 to 6; or g) a group of the formula:

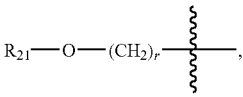

where $R^{21}$ is hydrogen; ($C_{1-8}$)alkyl; benzyl; or phenyl; in which the benzyl and phenyl groups are optionally mono- or independently di-substituted on the ring with $R^{12}$; and r is 0 or 2 to 6.

In accordance with another aspect of the invention, there are provided a group of cyclic beta compounds having the Formula (II):

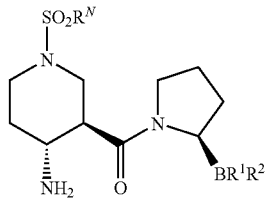

pharmaceutically acceptable salts thereof, stereomers thereof, tautomers thereof, prodrugs thereof, and solvates thereof. In a preferred embodiment the compound of Formula (II) is 90 wt % or more of a single enantiomer. In other preferred embodiments, the compounds of Formula (II) are 91, 92, 93, 94, 95, 96, 97, 98, or 99 wt % or more of a single enantiomer;

R[1] and R[2] independently or together are —OH, —O[−] M[+] wherein M[+] is a cation, a hydroxyl bearing a boronic acid protecting group, or a group capable of being hydrolyzed to a hydroxyl group in an aqueous solution at physiological pH or in biological fluids; and $R^N$ is a substituted or unsubstituted alkyl, alkenyl, aryl, aralkyl, cycloalkyl, cycloalkylalkyl, cycloalkenyl, cycloalkenylalkyl, heterocyclyl, or heterocyclylalkyl group. For example, $R^N$ can be a substituted phenyl group or a substituted or unsubstituted methyl, ethyl, n-propyl, isopropyl, n-butyl, isobutyl, sec-butyl, biphenyl, or naphthyl group. Exemplary $R^N$ groups include but are not limited to a 4-fluorophenyl, 3-fluorophenyl, 2-fluorophenyl, 2,4-difluorophenyl, 2,4,5-trifluorophenyl, or 4-methylsulfonylphenyl group.

By way of illustration only, the compounds of Formulas (I) and (II) include:
(2R)-1-[(3R,4R)-4-amino-1-benzenesulfonyl-piperidine-3-carbonyl]-boroPro-OH,
(2R)-1-[(3R,4R)-4-amino-1-methanesulfonyl-piperidine-3-carbonyl]-boroPro-OH,
(2R)-1-[(3R,4R)-4-amino-1-(4-fluoro-benzenesulfonyl)-piperidine-3-carbonyl]-boroPro-OH,
(2R)-1-[(3R,4R)-4-amino-1-(3-fluoro-benzenesulfonyl)-piperidine-3-carbonyl]-boroPro-OH,
(2R)-1-[(3R,4R)-4-amino-1-(2-fluoro-benzenesulfonyl)-piperidine-3-carbonyl]-boroPro-OH,
(2R)-1-[(3R,4R)-4-amino-1-(2,4-difluoro-benzenesulfonyl)-piperidine-3-carbonyl]-boroPro-OH,
(2R)-1-[(3R,4R)-4-amino-1-(2,4,5-trifluoro-benzenesulfonyl)-piperidine-3-carbonyl]-boroPro-OH,
(2R)-1-[(3R,4R)-4-amino-1-(4-methanesulfonyl-benzenesulfonyl)-piperidine-3-carbonyl]-boroPro-OH,
(2R)-1-[(3R,4R)-4-amino-1-(naphthalene-1-sulfonyl)-piperidine-3-carbonyl]-boroPro-OH,
(2R)-1-[(3R,4R)-4-amino-1-(naphthalene-2-sulfonyl)-piperidine-3-carbonyl]-boroPro-OH,
(2R)-1-[(3R,4R)-4-amino-1-(biphenyl-4-sulfonyl)-piperidine-3-carbonyl]-boroPro-OH,
(2R)-1-[(3R,4R)-4-amino-1-(biphenyl-3-sulfonyl)-piperidine-3-carbonyl]-boroPro-OH, and
(2R)-1-[(3R,4R)-4-amino-1-(propane-2-sulfonyl)-piperidine-3-carbonyl]-boroPro-OH.

A "pharmaceutically acceptable salt" includes a salt with an inorganic base, organic base (including basic amino acids), inorganic acid, organic acid (including acidic amino acids). As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid. Further examples of pharmaceutically acceptable salts include the pharmaceutically acceptable salts listed in Journal of Pharmaceutical Science, 66, 2 (1977) which are known to the skilled artisan.

The compounds of this invention may form solvates with standard low molecular weight solvents, including water to yield hydrates, using methods known to the skilled artisan.

It is to be understood that the invention extends to all of the stereoisomeric forms of the claimed compounds, including enantiomers and diastereomers, as well as the racemates.

Methods of Preparation of the Cyclic Beta Compounds of the Invention

The invention also relates to methods for preparing the above-described compounds. As shown below in Scheme I and as described in the Examples, the compounds of Formulas (I) and (II) can be prepared. A precursor to compounds of the invention may be prepared by reacting a pyrrolidine, suitably N-protected with a standard protecting group such as Boc-, Fmoc-, Cbz- or the like, with sec-BuLi/TMEDA followed by a boron source such as $B(OCH_3)_3$, to provide the boronic ester derivative. Acid hydrolysis of the methyl esters with 2N HCl provides the boronic acid intermediate. Reaction of the boronic acid with an alcohol, e.g., (+) pinanediol, deprotection of the amino protecting group, and recrystallization provides the pinanediol ester 1 as an isomerically pure salt. (See U.S. patent application Ser. No. 10/514,574, filed Nov. 15, 2004, entitled "Heterocyclic Boronic Acids.")

For example, as shown in Scheme I, compounds of Formulas (I) and (II) may be prepared by coupling the pyrrolidine 1 with an appropriate reagent, such as the suitably protected 4-aminopiperidine-3-carboxylic acid 2. Each nitrogen protecting group on the piperidine is orthogonal to the other. As shown in Scheme I, a suitable combination are the Boc and Cbz groups, but the invention is not so limited. Compound 2 may be synthesized by the method of Schinnerl M, Murray J K, Langenhan J M, Gellman S H. Eur. J. Org. Chem., 2003, 4:721-726. To prepare the coupled product 3, any standard method of forming an amide bond that leaves the stereochemistry at the 3-position of the piperidine undisturbed can be used. For example, suitable coupling methods include the use of coupling agents such as EDC/HOBt, DCC/HOBt, HATU, and the like; mixed anhydrides such as those formed from isobutyl chloroformate; acid fluorides; and others typically used in peptide synthesis. Compound 3, is selectively deprotected at the piperidine nitrogen to give 4 and sulfonylated with, e.g., a sulfonyl chloride bearing the RN group to provide comound 5. Deprotection of the 4-position amino group and hydrolysis of the boronic ester gives 6, a compound of Formulas (I) and (II). As should be understood, the choice of protecting groups and deprotection conditions used will depend on the particular compound being prepared and are well within the skill of the ordinary artisan in view of the present disclosure.

Scheme I

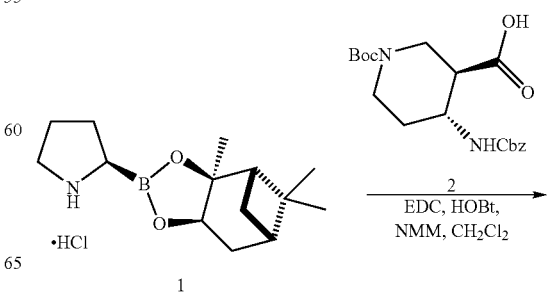

-continued

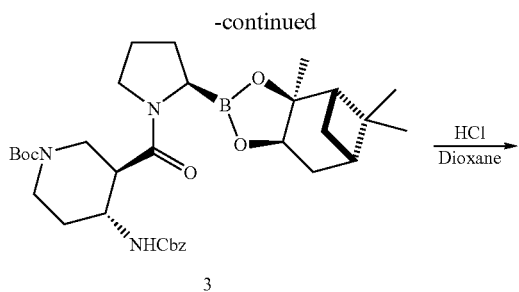

3

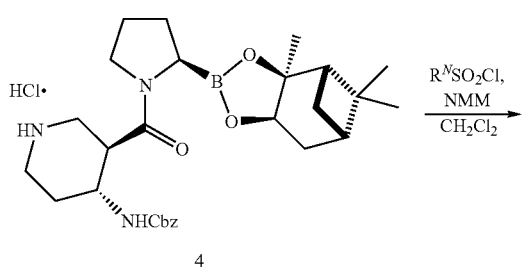

4

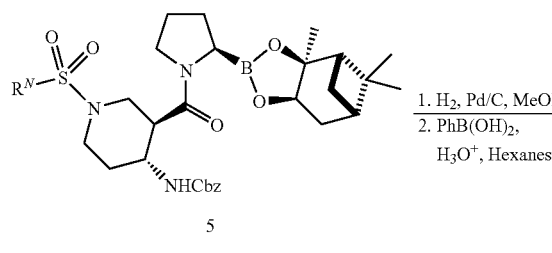

5

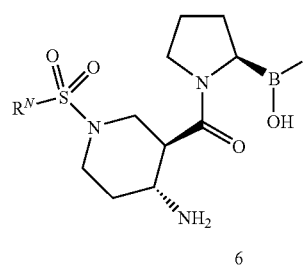

6

This synthetic scheme is adaptable for the preparation of all the compounds of Formula (II) of the invention, by reacting intermediate 4 with the appropriate sulfonylating agent. Such agents are commercially available (e.g., alkyl and aryl sulfonyl chlorides) or are easily synthesized through well-known procedures such as treating a sulfonic acid with thionyl chloride. In addition, it will be understood that other boronic ester groups may be used by, e.g., starting with a different alcohol or diol rather than pinanediol or removing the pinanediol group earlier in the synthesis and replacing it with another alcohol by analogous methods.

Thus, another aspect of the invention provides a process for preparing the compounds of Formula (II), the method comprising coupling a compound of Formula (IV) or an acid addition salt thereof:

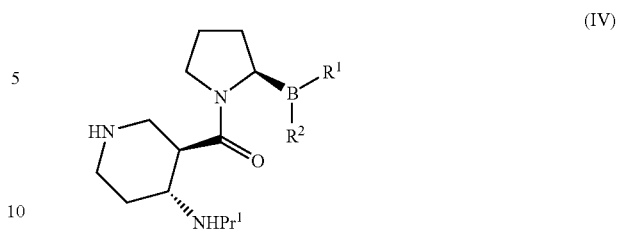

(IV)

with a compound of Formula (VI), $R^N$—$SO_2$-Q, optionally in the presence of a suitable base such as NMM, DIEA, TEA, pyridine, and the like; to provide a compound of Formula (II); wherein $Pr^1$ is a nitrogen-protecting group such as Boc, Cbz, Fmoc, benzyl, and the like; $R^1$ and $R^2$ independently or together are a group that can be hydrolyzed to hydroxyl; Q is a leaving group such as halogen (e.g. Cl, Br); and $R^N$ is as defined herein. Optionally, the resulting boronic ester of Formula (II) may be deprotected to recover the compound as a free acid or as a salt. In some embodiments, Q is halogen, including but not limited to Cl. In others $R^1$ and $R^2$ are each methoxy or together are pinanedioxy, e.g. (+)-pinanedioxy as in compound 3 above. In still others, Pr is Boc.

In yet another aspect of the invention, a process for preparing compounds of Formula (I) is provided. A method of preparing a compound of Formula (I)

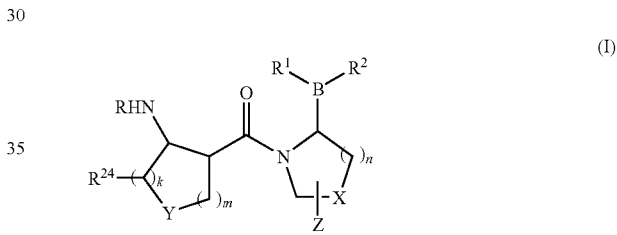

(I)

comprises contacting a compound of Formula (VIII)

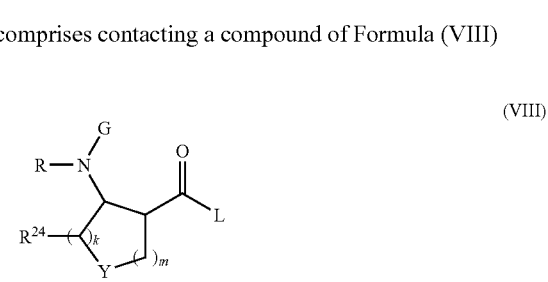

(VIII)

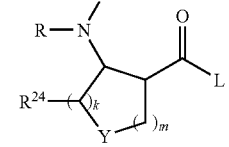

and a compound of Formula (IX):

(IX)

wherein G comprises a nitrogen protecting group and L comprises a leaving group. L is preferably chloro, bromo or a group generated from carboxylic acid activating agents such as isobutylchloroformate, DCC, EDCI and HOBT. The reaction is carried out under conditions suitable to provide a G protected compound of Formula (I), then treating the G protected compound of Formula (I) under conditions suitable to remove group G to provide the compound of Formula (I).

The pharmaceutically acceptable salts may be obtained as the direct products of compound synthesis. In the alternative, the free base may be dissolved in a suitable solvent containing the appropriate acid (or vice versa), and the salt isolated by evaporating the solvent or otherwise separating the salt and solvent.

Method/Use of a Cyclic Beta Compound of the Invention

The method of treatment and use of a cyclic beta compound of the invention is based upon inhibition of dipeptidyl peptidase-IV by contact of the enzyme, dipeptidyl peptidase-IV, with the compound in any of its forms as described above. The contact may be accomplished in vitro such as through a diagnostic test or a screening test, or in vivo through an appropriate administrative route as discussed below.

The in vivo methods according to the invention involve a compound of the invention in its role as a selective inhibitor of DPP-IV. For example, the invention provides a method of treatment of a mammal (such as a human) suffering from a malcondition that can be regulated or normalized via inhibition of DPP-IV such as any malcondition characterized by impaired glycemic control, especially Diabetes Mellitus and related conditions, by administering an effective amount of a compound of the invention to treat, control, ameliorate or prevent the malcondition. These malconditions are known to be the result, at least in part, of the presence, or altered activity, of peptides regulated by the enzyme DPP-IV, especially in the context of its physiological role in glycemic control. These methods of the invention are accomplished by administering to the mammal (e.g., a human) an effective amount of a compound of the invention. Treatment is affected by inhibition of DPP-IV. Administration is typically accomplished through use of a pharmaceutical composition containing a compound of the invention.

The method of the invention further includes a method for selectively inhibiting DPP-IV over related enzymes. In some embodiments of the methods for treatment, DPP-IV is inhibited by greater than 5-fold relative to one or more other dipeptidyl peptidases. In other embodiments, DPP-IV is inhibited by greater than 10-, 20-, or even 50-fold or more over other dipeptidyl peptidases. Exemplary other dipeptidyl peptidases include DPP-VII, DPP-VIII, DPP-IX, and FAP. For example, a compound of the invention can selectively inhibit DPP-IV over dipeptidyl peptidase-VII, or DPP-IV over dipeptidyl peptidase-VIII, or DPP-IV over dipeptidyl peptidase-IX, or DPP-IV over fibroblast activation protein (FAP). In additional embodiments, a compound of the invention selectively inhibits DPP-IV over dipeptidyl peptidase-VIII and fibroblast activation protein. In other embodiments, the compound of the invention selectively inhibits DPP-IV over dipeptidyl peptidase-VII, dipeptidyl peptidase-VIII, and fibroblast activation protein. This selectivity applies to in vitro and to in vivo situations. In particular, it has been determined in an in vivo protocol study in humans that a compound of the invention maintained selectivity for inhibition of DPP-IV over the other amino dipeptidyl peptidases. Preferably, the DPP-IV selectivity is shown relative to DPP-VIII. In some embodiments, the compounds of Formulas (I) and (II) inhibit DPP-IV over DPP-VIII by 10-fold or greater, e.g., 12-, 15-, 20-, 25-, 50-, or even 100-fold or greater.

For in vivo use as a DPP-IV inhibitor, a compound of the invention may be formulated in any manner as described herein and administered in an effective amount to a patient (human) suffering from a malcondition that can be regulated or normalized by inhibition of DPP-IV, especially a malcondition characterized by impaired glycemic control, especially Diabetes Mellitus and related conditions. For example, the malcondition can be Type 1 diabetes, Type 2 diabetes, gestational diabetes, MODY, impaired glucose tolerance, impaired fasting glucose, hyperglycemia, impaired glucose metabolism, impaired glucose tolerance (IGT) and its progression to Type II diabetes, hyperinsulinemia, obesity, beta cell degeneration (in particular apoptosis of beta cells), the progression of non-insulin-requiring Type II diabetes to insulin requiring Type II diabetes; loss of the number and/or the size of beta cells in a mammalian subject, and diabetic complications such as retinopathy, neuropathy, nephropathy, cardiomyopathy, dermopathy, diabetes related infection, atherosclerosis, coronary artery disease, stroke and similar malconditions.

In other embodiments of method of treatment according to the invention, insulin resistance is a component of the malcondition that can be regulated or normalized by inhibition of DPP-IV. For example, the malconditions can be impaired fasting glucose, impaired glucose tolerance, polycystic ovarian syndrome and the like. In yet other embodiments, the malcondition that can be regulated or normalized by inhibition of DPP-IV involves a decrease of islet neogenesis, β-cell survival, or insulin biosynthesis.

The administered dose of a compound of the invention will be carefully adjusted according to age, weight and condition of the patient, as well as the route of administration, dosage form and regimen and the desired result. The ultimate choice of dosage, route and pharmaceutical formulation will determined by the patient's attending physician, whose wisdom and judgment will guide this process. The dose for adults may range from about 0.5 to about 2,000 mg per day, preferably about 10 mg to about 1000 mg per day, more preferably about 50 mg to about 750 mg per day which can be administered in a single dose or in the form of multiple doses given up to 4 times per day.

The use of a compound of the invention also includes the manufacture of a medicine and a method of treatment using such a medicine in the form of a pharmaceutical composition.

Pharmaceutical Combinations and Their Use in Treatment

A cyclic beta compound of the invention may be combined with a second medicament to form a pharmaceutical combination of the invention. The second medicament is a known agent for treating, controlling, or preventing a malcondition that can be regulated or normalized via inhibition of DPP-IV. The malconditions treated by such combinations are those that can be regulated or normalized via inhibition of DPP-IV and thus are the same as those described above in connection with sole treatment for a cyclic beta compound of the invention.

The second medicament may include a therapeutically effective amount of a dipeptidyl peptidase-IV inhibitor other than the cyclic beta compound of the invention. The second medicament preferably may be a known anti-diabetic agent including but not limited to an agent that increases insulin secretion, an agent that increases insulin sensitivity, an agent that reduces the uptake of sugar from the gastrointestinal track, an agent that enhances the effect of endogenous peptides or proteins that play a role in glycemic control, or an agent that acts a replacement therapy for endogenous peptides or proteins that have a known role in glycemic control. Such agents include but are not limited to glyburide (e.g. Micronase® and Diabeta®), glipizide (e.g. Glucotrol®), nateglinide (e.g. Starlix®), repaglinide (e.g. Prandin®), metformin (e.g. Glucophage®), rosiglitazone (e.g. Avandia®), acarbose (e.g. Precose®), miglitol (e.g. Glyset®), exenatide (e.g. Byetta®), and insulin (e.g. Humulin® and Novolin®). Additional exemplary agents include but are not limited to biguanides, chlorpropamide, a glucagon-like peptide-1 (GLP-1) or mimetic thereof such as LY315902 or LY307161, glimepiride, meglitinide, phenformin, pioglitazone, sulfonyl ureas, troglitazone, Gl-262570, isaglitazone, JTT-501, NN-2344, L895645, YM-440, R-119702, AJ9677, KAD1129, APR-HO39242, GW-409544, KRP297, AC2993, Exendin-4, and NN2211. The chemical structures, trivial names and pharmacological studies of the foregoing compounds designated by letters and numbers are readily available from the web, for example, by entering the letter/number designation as a search term in the GOOGLE search web site.

A cyclic beta compound of the invention may be used in combination with one or more second medicaments useful as antidiabetic agents (employed to treat diabetes and related diseases). The second medicament may be administered orally in the same dosage with the compound of the invention, or in a separate oral dosage form. The compound of the invention and the second medicament may also be administered, for example by injection, separately, simultaneously or as a mixture.

The pharmaceutical combination of the invention can be formulated as a pharmaceutical composition comprising a pharmaceutically acceptable carrier along with a cyclic beta compound of the invention and one or more second medicaments.

In the pharmaceutical combination of the invention, the cyclic beta compounds of the invention are typically present in a weight ratio to the second medicament of from about 0.01:1 to about 100:1, or preferentially from about 0.1:1 to about 5:1.

The use of a cyclic beta compound of the invention in combination with one or more other antidiabetic agents may produce antihyperglycemic results greater than that possible from each of these antidiabetic agents alone. The use of a compound of the invention in combination with one or more other antidiabetic agents may also produce a synergistic effect in that the antihyperglycemic result may be greater than the combined additive antihyperglycemic effects produced by these antidiabetic agents.

The effective amount of a second medicament formulated as a component of the pharmaceutical combination of the invention will follow the recommendations of the second medicament manufacturer, the judgment of the attending physician and will be guided by the protocols and administrative factors for amounts and dosing as indicated in the PHYSICIAN'S DESK REFERENCE (PDR).

The administered dose of a compound of the invention within the pharmaceutical combination will be carefully adjusted according to age, weight and condition of the patient, as well as the route of administration, dosage form and regimen and the desired result. The ultimate choice of dosage, route and pharmaceutical formulation will determined by the patient's attending physician, whose wisdom and judgment will guide this process.

The compositions described above may be administered in the dosage forms as described above in single or divided doses of one to four times daily. It may be advisable to start a patient on a low dose combination and work up gradually to a high dose combination.

Pharmaceutical Compositions of the Invention

The invention includes a pharmaceutical composition containing a cyclic beta compound of the invention, with or without another medicament as described above, in association with a pharmaceutical carrier. The pharmaceutical composition can be formulated with one or more carriers such as conventional solid or liquid vehicles or diluents and pharmaceutical additives of a type appropriate to the mode of desired administration. The cyclic beta compound of the invention in a pharmaceutical composition can be administered to mammalian species, especially humans, by an oral, buccal, rectal, pulmonary or similar route, for example, in the form of tablets, capsules, granules or powders. It can be administered by a parenteral route in the form of injectable preparations. It can be administered by a transdermal route either by a release patch for transdermal delivery or by electro-transport using an appropriate delivery device.

Pharmaceutical compositions containing a cyclic beta compound of the invention of the invention may be prepared by conventional techniques, e.g. as described in Remington: The Science and Practice of Pharmacy, 19th Ed., 1995. The compositions may appear in conventional forms, for example capsules, tablets, aerosols, solutions, suspensions or topical applications.

A typical pharmaceutical composition includes a cyclic beta compound of the invention formulated with a pharmaceutically acceptable carrier which may be an excipient or a diluent, or may be enclosed within a carrier which can be in the form of a capsule, sachet, tablet, paper or other container. In making the composition, conventional techniques for the preparation of pharmaceutical compositions may be used.

For example, a cyclic beta compound of the invention will usually be mixed with a carrier, or diluted by a carrier, or enclosed within a carrier which may be in the form of an ampoule, capsule, tablet, sachet, paper, or other container. When the carrier serves as a diluent, it may be solid, semi-solid, or liquid material that acts as a vehicle, excipient, or medium for the active compound. The cyclic beta compound can be adsorbed on a granular solid container for example in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax.

A formulation can be mixed with auxiliary agents which do not deleteriously react with the compound. Such additives can include wetting agents, emulsifying and suspending agents, salt for influencing osmotic pressure, buffers, coloring substances, preserving agents, sweetening agents or flavoring agents. A pharmaceutical composition can also be sterilized if desired.

The route of administration may be any route, which effectively transports the compound of the invention to the appropriate or desired site of action, such as oral, nasal, pulmonary, buccal, rectal, subdermal, intradermal, transdermal or depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is non-volatile, including natural or synthetic oils, fatty acids, mono-, di- or tri-glycerides.

For injection, a pharmaceutical composition may be a powder suitable for reconstitution with an appropriate solution as described above. Examples of these include, but are not limited to, freeze dried, rotary dried or spray dried powders, amorphous powders, granules, precipitates, or particulates. For injection, a pharmaceutical composition may optionally contain stabilizers, pH modifiers, surfactants, bioavailability modifiers and combinations of these. A compound of the invention may be formulated for parenteral administration by injection such as by bolus injection or continuous infusion. A unit dosage form for injection may be in ampoules or in multi-dose containers.

A pharmaceutical composition of the invention may be designed to provide quick, sustained, or delayed release of the active ingredient after administration to the patient by employing procedures well known in the art. Thus, a pharmaceutical composition may also be formulated for controlled release or for slow release.

A pharmaceutical composition of the invention may include, for example, micelles or liposomes, or some other encapsulated form, or may be administered in an extended release form or an enteric coated form to provide a prolonged storage and/or delivery effect. Therefore, the pharmaceutical composition may be compressed into pellets or cylinders and implanted intramuscularly or subcutaneously as depot injections or as implants such as stents. Such implants may employ known inert materials such as silicones and biodegradable polymers, e.g., polylactide-polyglycolide. Examples of other biodegradable polymers include poly-orthoesters and poly-anhydrides.

A cyclic beta compound of the invention may be formulated as a sustained release implant or implantable material suitable for continuous administration over a significant period of time. Typical sustained release implants are formed from polymers of pharmaceutically acceptable, biodegradable polymers such as polymers and copolymers of lactic acid, lactide, glycolic acid, glycolide, caproic acid and caprolactone. The dose and amount of compound of the invention within the implant will be calculated to deliver the desired single dose blood level of compound.

For nasal administration, a pharmaceutical composition may contain a cyclic beta compound of the invention dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with a cyclic beta compound of the invention dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that may be prepared by conventional tabletting techniques may contain:

| Core: | |
|---|---|
| Cyclic Beta Compound of the invention* | 300 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Adde |
| Coating: | |
| HPMC approx. | 9 mg |
| **Mywacett 9-40 T approx. | 0.9 mg |

*Compound is formulated as free compound or salt thereof.
**Acylated monoglyceride used as plasticizer for film coating.

A typical capsule for oral administration contains a cyclic beta compound of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compound of the invention into a vial, aseptically freeze-drying and sealing. For use, the contents of the vial are mixed with 2 mL of physiological saline, to produce an injectable preparation.

A cyclic beta compound of the invention may be administered to a mammal, especially a human in need of such treatment, prevention, elimination, alleviation or amelioration of the various malconditions mentioned above. Such mammals include also animals, both domestic animals, e.g. household pets, farm animals, and non-domestic animals such as wildlife.

A cyclic beta compound of the invention is effective over a wide dosage range. For example, in the treatment of adult humans, dosages from about 0.5 to about 2000 mg, preferably from about 10 mg to about 1000 mg, per day, more preferably about 50 to 750 mg per day may be used. A typical dosage is about 50 mg to about 750 mg per day. In choosing a regimen for patients it may frequently be necessary to begin with a higher dosage and when the condition is under control to reduce the dosage. The exact dosage will depend upon the mode of administration, on the therapy desired, form in which administered, the subject to be treated and the body weight of the subject to be treated, and the preference and experience of the physician or veterinarian in charge.

Generally, a cyclic beta compound of the invention is dispensed in unit dosage form including from about 0.5 to about 2000 mg of active ingredient together with a pharmaceutically acceptable carrier per unit dosage.

Usually, a dosage form suitable for oral, nasal, pulmonary or transdermal administration includes from about 0.5 mg to about 2000 mg, preferably from about 10 mg to about 1000 mg per day, more preferably from about 50 mg to about 750 mg of a compound admixed with a pharmaceutically acceptable carrier or diluent.

A pharmaceutical combination of the invention may be formulated as a pharmaceutical composition employing all of the embodiments, carriers, route designs and the like described above for formulation of a pharmaceutical composition of a compound alone.

The invention also encompasses prodrugs of a cyclic beta compound of the invention which on administration undergo chemical conversion by metabolic processes before becoming active pharmacological substances. In general, such prodrugs will be functional derivatives of a compound of the invention which are readily convertible in vivo into a compound of the invention. Conventional procedures for the selection and preparation of suitable prodrug derivatives are described, for example, in "Design of Prodrugs", ed. H. Bundgaard, Elsevier, 1985.

The invention also encompasses active metabolites of a cyclic beta compound of the invention.

Thus, another aspect of the invention provides a pharmaceutical composition of a cyclic beta compound of the invention, alone or in combination with another type antidiabetic agent and/or other type therapeutic agent.

Additional embodiments of the invention are represented by:
A pharmaceutical composition including a cyclic beta compound of the invention, as described above, together with at least one pharmaceutically acceptable carrier or diluent;
Methods of making a pharmaceutical composition of a cyclic beta compound of the invention wherein the pharmaceutically acceptable carrier or diluent is suitable for oral administration;
Methods of making a pharmaceutical composition of a cyclic beta compound of the invention suitable for oral administration further including the step of formulating the composition into a tablet or capsule;
Methods of making a pharmaceutical composition of a cyclic beta compound of the invention wherein the pharmaceutically acceptable carrier or diluent is suitable for parenteral administration;
Methods of making a pharmaceutical composition of a cyclic beta compound of the invention suitable for parenteral administration further including the step of lyophilizing the composition to form a lyophilized preparation.

DPP-IV inhibitory activity of the cyclic beta compound of the invention may be determined by use of an in vitro assay system. Inhibition constants (Ki or IC50 values) for the DPP-IV inhibitors of the invention may be determined by the method described below.

A further detailed description of the invention is given with reference to the following non-limiting examples. All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

EXAMPLES

The following abbreviations are used herein and throughout the disclosure:
DCC: Dicyclohexylcarbodiimide
DCM: Dichloromethane
DIEA: N,N-Diisopropylethylamine
DMF: N,N-Dimethylformamide
DMSO: Dimethylsulfoxide
EDC: 1-ethyl-3-(3'-dimethylaminopropyl)carbodiimide hydrochloride
EtOAc: Ethyl acetate
$Et_3N$, TEA: Triethylamine
HATU: 2-(7-Aza-1H-benzotriazole-1-yl)-1,1,3,3-tetramethyluronium hexafluorophosphate
HOBt: 1-Hydroxybenzotriazole
MeOH: Methanol
mL: Milliliter
mmol: Millimole(s)
MS: Mass spectroscopy
NMM: N-methylmorpholine
NMR: Nuclear magnetic resonance
TFA: Trifluoroacetic acid
μL: microliter

Example 1

Synthesis of Compounds of the Invention (2R)-1-[(3R,4R)-4-benzyloxycarbonylamino-1-tert-Butoxycarbonyl-piperidine-3-carbonyl]-boroPro-(1S, 2S,3R,5S)-pinanediol ester (3)

To a solution of (3R,4R)-4-Benzyloxycarbonylamino-piperidine-1,3-dicarboxylic acid 1-tert-butyl ester 2 (250 mg, 0.66 mmol) in $CH_2Cl_2$ (7 mL) and DMF (1 mL) was added HOBt (101 mg, 0.7 mmol) and EDC (152 mg, 0.8 mmol). The reaction solution was then cooled to 0° C. in an ice bath for 10 min followed by sequential addition of boroPro-(1S,2S,3R, 5S)-pinanediol ester 1 (207 mg, 0.7 mmol; prepared as in, e.g., U.S. patent application Ser. No. 10/514,574, filed Nov. 15, 2004, entitled "Heterocyclic Boronic Acids") and NMM (0.22 mL, 2 mmol). The reaction solution was allowed to warm up to room temperature and stirred overnight. The reaction mixture was diluted with additional $CH_2Cl_2$ (5 mL) and water (8 mL). The organic layer was dried over $Na_2SO_4$ and evaporated under reduced pressure. The resulting oily residue was purified by column chromatography (silica gel, solvent eluent gradient from 1:5 EtOAc/hexane to 2:1 EtOAc/hexane) to afford 3 (311 mg, 0.51 mmol) in 77% yield as a clear viscous oil. MS m/z (rel intensity) 632 (M+23)+(3), 610 (M+1)+(100), 554 (31).

(2R)-1-[(3R,4R)-4-benzyloxycarbonylamino-piperidine-3-carbonyl]-boroPro-(1S,2S,3R,5S)-pinanediol ester hydrochloride salt (4)

A solution of compound 3 (152 mg, 0.25 mml) in 4N HCl in dioxane (3 mL) was stirred at room temperature for 3 h. The solvent was removed under vacuum and the resulting residue used in the next step without further purification. MS m/z (rel intensity) 510 (M+1)$^+$(100), 358 (15), 207 (7).

(2R)-1-[(3R,4R)-1-Benzenesulfonyl-4-benzyloxycarbonylamino-piperidine-3-carbonyl]-boroPro-(1S,2S, 3R,5S)-pinanediol ester (5)

To a solution of 4 in $CH_2Cl_2$ (4 mL) cooled to 0° C. was sequentially added NMM (110 μL, 1 mmol) and benzenesulfonyl chloride (64 μL, 0.5 mmol). The reaction mixture was allowed to warm up to room temperature and stir for 1.5 hours. The reaction was then diluted with $CH_2Cl_2$ (2 ml) and water (4 mL). The organic phase was isolated and dried over $MgSO_4$. After filtration, solvents were removed under reduced pressure. The oily residue was purified by column chromatography (silica gel) using a mixture of EtOAc/Hexanes as eluent. Compound 5 (38.4 mg, 0.06 mmol) was obtained in 24% yield for the two consecutive steps. MS m/z (rel intensity) 650 (M+1)$^+$(100), 498 (57).

(2R)-1-[(3R,4R)-4-amino-1-Benzenesulfonyl-piperidine-3-carbonyl]-boroPro-OH (6)

To a solution of compound 5 (26.9 mg, 0.04 mmol) in MeOH (6 mL) was added 10% Pd/C (28 mg). The mixture was stirred under a $H_2$ atmosphere for 1.5 h. Upon completion of the reaction, it was filtered through a plough of Celite. The solvents were removed under reduced pressure and the resulting residue used in the next step without further purification.

To a solution of the crude obtained above in $H_2O$ (2 mL) adjusted to pH 2 by addition of 4 N HCl in water was added hexane (2 mL) and phenyl boronic acid (11 mg, 0.04 mmol). The bi-phasic mixture was stirred vigorously. The hexane layer was periodically removed and replaced with fresh hexane 6 times over a 24-hour period. The aqueous layer was separated and applied to a Dowex 50-X2-100 ion exchange column (H+ form) and eluted with water until the eluate was neutral. Elution with aqueous ammonium hydroxide (2% vbw) followed by lyophilization of the appropriate fractions yielded compound 6 (11.3 mg, 0.03 mmol) in 75% yield for the two consecutive steps as a white crystalline solid. 6-TFA salt $^1$H-NMR (500 MHz, $D_2O$) δ 7.73 (m, 2H), 7.63 (m, 1H), 7.54 (m, 2H), 3.96 (m, 1H), 3.84 (m, 1H), 3.54 (m, 1H), 3.37 (m, 1H), 2.84 (m, 1H), 2.56 (ddd, J=12.8, 12.8, 2.5 Hz, 1H), 2.42 (dd, J=12.8, 11.3 Hz, 1H), 1.98 (m, 3H), 1.84 (m, 1H), 1.63 (m, 1H), 1.56 (m, 1H). MS m/z (rel intensity) 727 (8), 364 (M−17)(56), 336 (8), 152 (100).

Example 2

Using the procedures illustrated above, the following compounds in the Table 1 were prepared and characterized using liquid chromatography-mass spectroscopy (LC-MS).

TABLE 1

| Compound No. | Name | Structure | LC-MS |
|---|---|---|---|
| 6 | (2R)-1-[(3R,4R)-4-amino-1-Benzenesulfonyl-piperidine-3-carbonyl]-boroPro-OH | 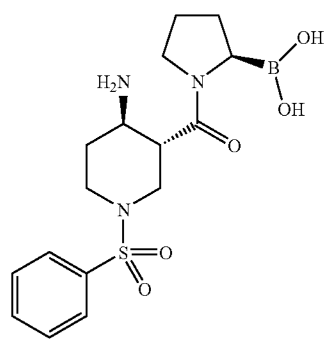 | 727(8), 364 (M-17)(56) |
| 7 | (2R)-1-[(3R,4R)-4-amino-1-methanesulfonyl-piperidine-3-carbonyl]-boroPro-OH | 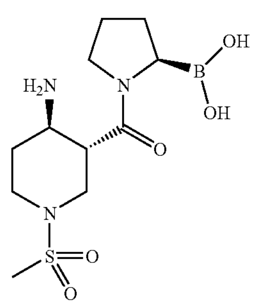 | 603(24), 302 (M-17)(73) |
| 8 | (2R)-1-[(3R,4R)-4-amino-1-(4-fluoro-benzenesulfonyl)-piperidine-3-carbonyl]-boroPro-OH | 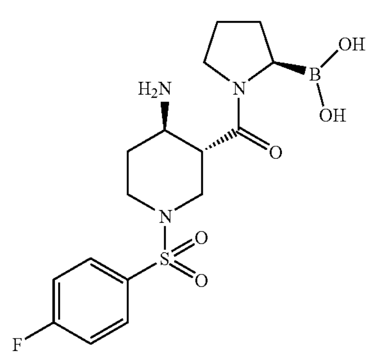 | 763(3), 382 (M-17)(2) |

TABLE 1-continued

| Compound No. | Name | Structure | LC-MS |
|---|---|---|---|
| 9 | (2R)-1-[(3R,4R)-4-amino-1-(3-fluoro-benzenesulfonyl)-piperidine-3-carbonyl]-boroPro-OH | 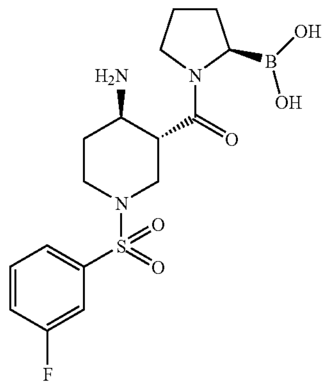 | 763(4), 382 (M-17)(3) |
| 10 | (2R)-1-[(3R,4R)-4-amino-1-(2-fluoro-benzenesulfonyl)-piperidine-3-carbonyl]-boroPro-OH | 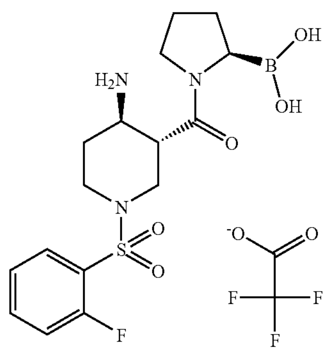 | 763(2), 382 (M-17)(3) |
| 11 | (2R)-1-[(3R,4R)-4-amino-1-(2,4-difluoro-benzenesulfonyl)-piperidine-3-carbonyl]-boroPro-OH | 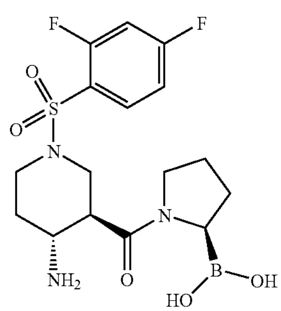 | 400 (M-17)(6), 345 (27) |
| 12 | (2R)-1-[(3R,4R)-4-amino-1-(2,4,5-trifluoro-benzenesulfonyl)-piperidine-3-carbonyl]-boroPro-OH | 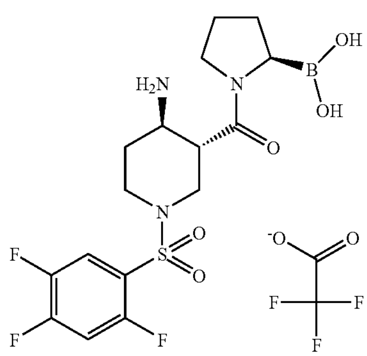 | 363 (10), 152 (100) |

TABLE 1-continued

| Compound No. | Name | Structure | LC-MS |
|---|---|---|---|
| 13 | (2R)-1-[(3R,4R)-4-amino-1-(4-methanesulfonyl-benzenesulfonyl)-piperidine-3-carbonyl]-boroPro-OH | 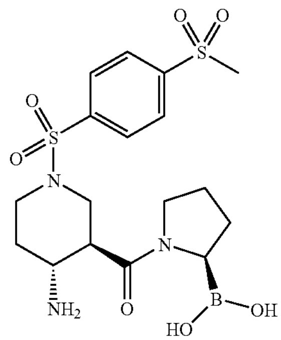 | 442 (M-17)(5), 387 (24) |
| 14 | (2R)-1-[(3R,4R)-4-amino-1-(naphthalene-1-sulfonyl)-piperidine-3-carbonyl]-boroPro-OH | 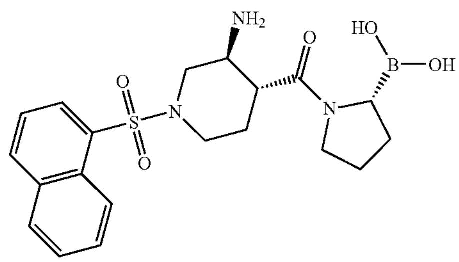 | 414 (M-17)(10), 152 (100) |
| 15 | (2R)-1-[(3R,4R)-4-amino-1-(naphthalene-2-sulfonyl)-piperidine-3-carbonyl]-boroPro-OH | 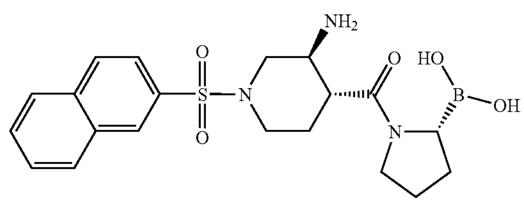 | 414 (M-17)(5), 152 (100) |
| 16 | (2R)-1-[(3R,4R)-4-amino-1-(biphenyl-4-sulfonyl)-piperidine-3-carbonyl]-boroPro-OH | 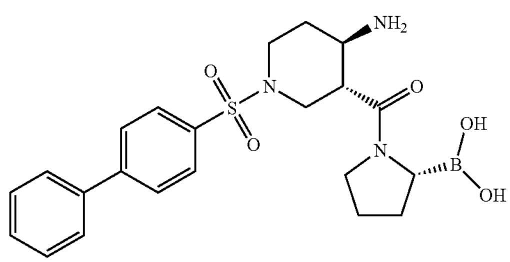 | 440 (M-17)(4), 152 (100) |
| 17 | (2R)-1-[(3R,4R)-4-amino-1-(biphenyl-3-sulfonyl)-piperidine-3-carbonyl]-boroPro-OH | 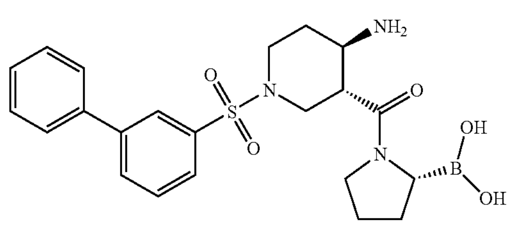 | 440 (M-17)(8), 152 (100) |

TABLE 1-continued

| Compound No. | Name | Structure | LC-MS |
|---|---|---|---|
| 18 | (2R)-1-[(3R,4R)-4-amino-1-(propane-2-sulfonyl)-piperidine-3-carbonyl]-boroPro-OH | 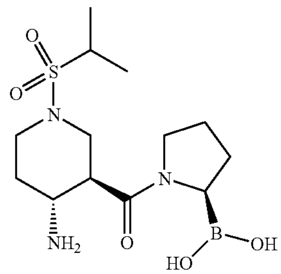 | 330 (M-17)(5), 152 (100) |

Example 3

Compounds for comparative examples are listed in Table 2. Such compounds may be prepared by procedures known in the art in view of the present disclosure. For example, the protected boroproline intermediate 1 may be acylated with chloroacetyl chloride and the chlorine group displaced with the appropriate amine to give 19, 20 or 21.

TABLE 2

| Compound No. | Structure | LC-MS |
|---|---|---|
| 19 | 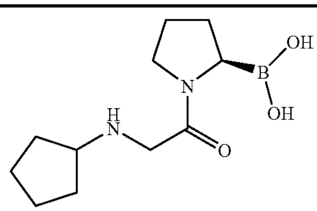 | N/A |
| 20 | 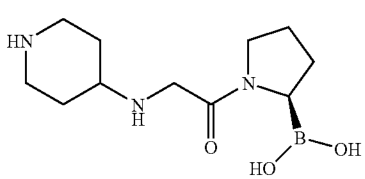 | 256 (M + 1) (100) |
| 21 | 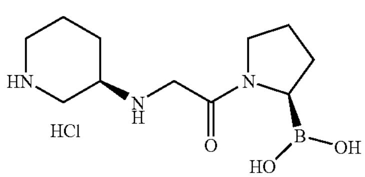 | 256 (M + 1) (100), 238(8) |

Example 4

Methods For Measuring DPP-IV Activity

The following methods were used to measure the activities of the compounds of the invention which inhibit the enzymatic activity of DPP-IV. The compounds of the invention are tested for their ability to inhibit the enzyme activity of purified DPP-IV. Briefly, the activity of DPP-IV is measured in vitro by its ability to cleave the synthetic substrate Gly-Pro-AMC. Cleavage of Gly-Pro-AMC by DPP-IV liberates the product AMC (7-amino-4-methyl coumarin), whose rate of appearance is directly proportional to the enzyme activity. Inhibition of the enzyme activity by specific enzyme inhibitors slows down the generation of AMC. Stronger interaction between an inhibitor and the enzyme results in a slower rate of generation of AMC. Thus, the degree of inhibition of the rate of accumulation of AMC is a direct measure of the strength of enzyme inhibition. The accumulation of AMC is measured fluorometrically. The inhibition constant, Ki, or the $IC_{50}$ (concentration of test compound at which 50% of the enzyme activity is inhibited) for each compound is determined by incubating fixed amounts of enzyme with several different concentrations of inhibitor and substrate.

Thus, DPP-IV enzyme activity was determined by a fluorometric assay with the substrate Gly-Pro-AMC which is cleaved by DPP-IV to release the fluorescent AMC leaving group. Free AMC (7-amino-4-methyl coumarin) was measured using an excitation wavelength of 380 nm and an emission wavelength of 460 nm with a Victor-II fluorescent reader. Stock solutions of DPP-IV (1 ng/µl, pH 8.0) and Gly-Pro-AMC substrate (400 µM) in 25 mM Tris buffer (pH 8.0) were prepared separately. Test compounds were dissolved in DMSO or in 50 mM glycine buffer (pH 3.0). The assay was performed by diluting the DPP-IV stock (10 µl) into 25 mM Tris buffer (77.5 µl) followed by addition of test compound (2.5 µl) at 26° C. After 10-minutes substrate was added (10 µl) and allowed to react for 20-minutes at 26° C. before free AMC was measured. $IC_{50}$ values were determined in triplicate, using a minimum of six different inhibitor concentrations. $IC_{50}$ values were calculated using Nonlinear Regression Analysis (GraphPad, Prism, San Diego, Calif.).

The purification of porcine DPP-IV and the enzyme assay under steady state conditions are described in (1) Rahfeld, J. Schutkowski, M., Faust, J., Neubert., Barth, A., and Heins, J. (1991) Biol. Chem. Hoppe-Seyler, 372, 313-318; and (2) Nagatsu, T., Hino, M., Fuyamada, H., Hayakawa, T., Sakakibara, S., Nakagawa, Y., and Takemoto, T. (1976) Anal. Biochem., 74, 466-476, respectively. DPP-IV is also commercially available from, e.g., Research Diagnostics. The final compounds of Examples 1-3 were tested in vitro as inhibitors of DPP-IV as described herein and each displayed an $IC_{50}$ and/or $K_i$ of 1 µM or less.

Example 5

Methods for Measuring Activity of DPP-VII, DPP-VIII, DPP-IX, and FAP

Materials. S9 insect cells and Sf-900 II SFM media were from Invitrogen. Anti-FLAG M2 immunoaffinity gel was from Sigma. Gly-Pro-AMC, Lys-Pro AMC, and Ala-Pro AMC were from Enzyme Systems. $IC_{50}$ calculations were performed by non-linear regression analysis using Prism software (GraphPad).

Preparation of DPP-VII, DPP-VIII, DPP-IX, and FAP baculovirus constructs. The full length cDNAs for human DPP-VII, DPP-VIII, DPP-IX, and FAP were obtained from Open Biosystems. The cDNAs were cloned into the pFastBac vector with the addition of an N-terminal FLAG tag on DPP-VII, C-terminal 6xHis tags on DPP-VIII and DPP-IX, and an N-terminal 6xHis tag on FAP (Sun 2002, Qi 2003, and Chen 2004). Baculovirus was prepared using the Bac-to-Bac Baculovirus Expression System (Invitrogen). The cDNAs in the final baculovirus constructs were sequence verified.

Baculovirus expression. S9 cells were grown to mid log phase at 27C with shaking at 125 RPM and then adjusted to 2×10E6/ml just prior to baculovirus infection. Infection with DPP-VII, DPP-VIII, DPP-IX, and FAP baculoviral constructs were all performed at an MOI of 4. The infected cells were grown for 48 hours and the cell pellets harvested and frozen until purification. DPP-VII was purified using anti-FLAG immunoaffinity gel according to the manufacturer's instructions. DPP-VIII, DPP-IX, and FAP were purified using a B-PER 6xHis Fusion Protein Column Purification Kit from Pierce.

$IC_{50}$ assay. Recombinant DPPs were diluted in reaction buffer to give fluorescence values of 5000-20000 counts in the "enzyme only wells" 20 min after addition of substrate at 27° C. Reaction buffers were 25 mM (2-(4-Morpholino)-Ethane Sulfonic Acid), pH 5.5 for DPP-VII, 25 mM Tris, pH 8, 1% Triton X-100, 100 mM NaCl for DPP-VIII, and 25 mM Tris pH 8 for DPP-1× and FAP. Test wells in a 96-well microtiter plate contained 88 μL of diluted DPP and 2.5 ul of titrated compound in 50 mM glycine, pH 2.6. "Enzyme only" wells contained 88 uL of diluted DPP and 2.5 ul of glycine buffer. "No enzyme" wells contained 88 uL of reaction buffer without DPP and 2.5 ul of glycine buffer. All assays were done in triplicate. The plate was incubated at 27° C. for 10 min and then cooled on ice for 10 min. Ten microliters of substrate diluted in reaction buffer (40 uM final concentration) without Triton or NaCl were then added to all wells followed by incubation at 27C for 20 min. Substrates were Lys-Pro AMC for DPP-VII, and Ala-Pro AMC for DPP-VIII, DPP-IX, and FAP. Fluorescence in each well was measured at settings of 380/460 nm.

Compounds of the invention were tested for inhibition of DPP-IV according to Example 4 and DPP-VII, VIII, IX and FAP according to the present methods. Results are shown in Table 3.

TABLE 3

| Compound No. | Selectivity Ratios* | | |
|---|---|---|---|
| | DPP-VII | DPP-VIII | FAP |
| 6 | E | D | E |
| 7 | E | C | E |
| 8 | E | D | D |
| 9 | E | D | D |
| 10 | E | C | D |
| 11 | E | D | E |
| 12 | C | C | C |
| 13 | E | D | E |
| 14 | C | C | C |
| 15 | D | D | C |
| 16 | E | E | C |
| 17 | C | E | C |

TABLE 3-continued

| Compound No. | Selectivity Ratios* | | |
|---|---|---|---|
| | DPP-VII | DPP-VIII | FAP |
| 18 | C | C | D |
| 19 | A | B | B |
| 20 | A | B | E |
| 21 | A | B | C |

*Selectivity ratios: $A \leq 1$; $1 < B \leq 10$; $10 < C \leq 50$; $50 < D \leq 100$; $E > 100$.

As shown in Table 3, examples 6-18 of the claimed compounds demonstrate unexpected selectively towards the other dipeptidyl peptidases while maintaining potency against DPP-IV. In particular each of the compounds show excellent selectivity for DPP-IV relative to DPP-VIII. By comparison, examples 19-21, which also contain the boroproline moiety, show little or no selectively for DPP-IV over related enzymes. As shown in Example 6 and by others (Webber A E, et. al. 64th American Diabetes Association Conference 2004, Poster #1415), inhibition of DPP-VIII (and possibly DPP-IX) has been tied to debilitating side-effects in animal studies. Therefore, compounds of the invention are expected to show a much lower incidence of DPP-VIII mediated side-effects in vivo.

Example 6

In Vivo Toxicity of Non-Selective Boronic Acids

Toxicity in Rats: The Zucker Diabetic Fatty (ZDF) rat model can be used to investigate the effects of the compounds of the invention on both the treatment and prevention of diabetes as rats of this sub-strain are initially pre-diabetic although they develop severe type 2 diabetes characterized by increased HbA1c levels over a period of 6 weeks. The same strain can be used to predict the clinical efficacy of other anti-diabetic drug types. For example, the model predicts the potency and limited clinical efficacy of thiazolidinedione insulin sensitizer compounds. The experimental protocol requires p.o. (oral gavage) administration of either vehicle or test article at indicated doses either QD or BID using a gastric feeding needle with a ball tip, without anesthesia, using hand restraint to adult rats which have been fasted overnight. Animals are monitored for clinical signs at 1, 2, 4 and 8 hour time intervals following the treatment regimen. Whole blood samples (to a maximum level of 10% of the total blood volume every 2 weeks) were collected from the animals from the retro-orbital sinus in accordance with the guidelines of the IACUC committee. Comparative compound 19, a potent inhibitor of DPP-IV was orally dosed according to the protocol.

Oral doses of compound 19 (5-10 mg/kg) and PT100 (1 mg/kg) caused acute toxicity (death) 4-24 hrs post-dose in all Zucker Obese Fatty rats tested. The expected therapeutic dose level could not be reached for the comparative compounds before acute toxicity was observed.

Toxicity in Dogs: Oral dosing studies in dogs were carried out to further demonstrate the improved safety of compounds of the invention over non-selective inhibitors of DPP-IV. Compound 19 is a potent inhibitor of DPP-IV, VIII and IX.

In an escalated oral dose study in dogs, compound 19 showed increasing toxicity until at 2.0 mg/kg the dog exhibited severe emesis and diarrhea within 2-4 hours of dosing. The 2.0 mg/kg dose of compound 19 correlated with the time above the DPP-VIII $IC_{90}$ but not with the time above DPP-IX $IC_{90}$. By comparison, a previously known selective inhibitor (compound 10 in U.S. patent application Ser. No. 10/514,574, filed Nov. 15, 2004, entitled "Heterocyclic Boronic Acids") showed no toxicity at three times the dose of compound 19, the data are consistent with the toxicity being caused by inhibition of DPP-VIII rather than DPP-IV or DPP-IX.

While the invention has been described and exemplified in sufficient detail for those skilled in this art to make and use it, various alternatives, modifications, and improvements will be apparent to those skilled in the art without departing from the spirit and scope of the claims. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

Other embodiments are set forth within the following claims.

What is claimed is:

1. A compound selected from the group consisting of:
    (2R)-1-[(3R,4R)-4-amino-1-benzenesulfonyl-piperidine-3-carbonyl]-boroPro-OH,
    (2R)-1-[(3R,4R)-4-amino-1-methanesulfonyl-piperidine-3-carbonyl]-boroPro-OH,
    (2R)-1-[(3R,4R)-4-amino-1-(4-fluoro-benzenesulfonyl)-piperidine-3-carbonyl]-boroPro-OH,
    (2R)-1-[(3R,4R)-4-amino-1-(3-fluoro-benzenesulfonyl)-piperidine-3-carbonyl]-boroPro-OH,
    (2R)-1-[(3R,4R)-4-amino-1-(2-fluoro-benzenesulfonyl)-piperidine-3-carbonyl]-boroPro-OH,
    (2R)-1-[(3R,4R)-4-amino-1-(2,4-difluoro-benzenesulfonyl)-piperidine-3-carbonyl]-boroPro-OH,
    (2R)-1-[(3R,4R)-4-amino-1-(2,4,5-trifluoro-benzenesulfonyl)-piperidine-3-carbonyl]-boroPro-OH,
    (2R)-1-[(3R,4R)-4-amino-1-(4-methanesulfonyl-benzenesulfonyl)-piperidine-3-carbonyl]-boroPro-OH,
    (2R)-1-[(3R,4R)-4-amino-1-(naphthalene-1-sulfonyl)-piperidine-3-carbonyl]-boroPro-OH,
    (2R)-1-[(3R,4R)-4-amino-1-(naphthalene-2-sulfonyl)-piperidine-3-carbonyl]-boroPro-OH,
    (2R)-1-[(3R,4R)-4-amino-1-(biphenyl-4-sulfonyl)-piperidine-3-carbonyl]-boroPro-OH,
    (2R)-1-[(3R,4R)-4-amino-1-(biphenyl-3-sulfonyl)-piperidine-3-carbonyl]-boroPro-OH, and
    (2R)-1-[(3R,4R)-4-amino-1-(propane-2-sulfonyl)-piperidine-3-carbonyl]-boroPro-OH.

2. The compound of claim 1, wherein the compound is (2R)-1-[(3R,4R)-4-amino-1-benzenesulfonyl-piperidine-3-carbonyl]-boroPro-OH.

3. The compound of claim 1, wherein the compound is (2R)-1-[(3R,4R)-4-amino-1-methanesulfonyl-piperidine-3-carbonyl]-boroPro-OH.

4. The compound of claim 1, wherein the compound is (2R)-1-[(3R,4R)-4-amino-1-(4-fluoro-benzenesulfonyl)-piperidine-3-carbonyl]-boroPro-OH.

5. The compound of claim 1, wherein the compound is (2R)-1-[(3R,4R)-4-amino-1-(3-fluoro-benzenesulfonyl)-piperidine-3-carbonyl]-boroPro-OH.

6. The compound of claim 1, wherein the compound is (2R)-1-[(3R,4R)-4-amino-1-(2-fluoro-benzenesulfonyl)-piperidine-3-carbonyl]-boroPro-OH.

7. The compound of claim 1, wherein the compound is (2R)-1-[(3R,4R)-4-amino-1-(2,4-difluoro-benzenesulfonyl)-piperidine-3-carbonyl]-boroPro-OH.

8. The compound of claim 1, wherein the compound is (2R)-1-[(3R,4R)-4-amino-1-(2,4,5-trifluoro-benzenesulfonyl)-piperidine-3-carbonyl]-boroPro-OH.

9. The compound of claim 1, wherein the compound is (2R)-1-[(3R,4R)-4-amino-1-(4-methanesulfonyl-benzenesulfonyl)-piperidine-3-carbonyl]-boroPro-OH.

10. The compound of claim 1, wherein the compound is (2R)-1-[(3R,4R)-4-amino-1-(naphthalene-1-sulfonyl)-piperidine-3-carbonyl]-boroPro-OH.

11. The compound of claim 1, wherein the compound is (2R)-1-[(3R,4R)-4-amino-1-(naphthalene-2-sulfonyl)-piperidine-3-carbonyl]-boroPro-OH.

12. The compound of claim 1, wherein the compound is (2R)-1-[(3R,4R)-4-amino-1-(biphenyl-4-sulfonyl)-piperidine-3-carbonyl]-boroPro-OH.

13. The compound of claim 1, wherein the compound is (2R)-1-[(3R,4R)-4-amino-1-(biphenyl-3-sulfonyl)-piperidine-3-carbonyl]-boroPro-OH.

14. The compound of claim 1, wherein the compound is (2R)-1-[(3R,4R)-4-amino-1-(propane-2-sulfonyl)-piperidine-3-carbonyl]-boroPro-OH.

15. The pharmaceutical composition comprising a compound of claim 1 and a pharmaceutically acceptable carrier.

16. A composition comprising a selective DPP-IV inhibitory effective amount of a compound of claim 1 and a pharmaceutically acceptable carrier.

17. The method of treating hyperglycemia comprising administering to a mammal in need thereof an effective amount of a compound of claim 1.

18. The method of claim 17, wherein the hyperglycemia is in diabetes.

* * * * *